(12) United States Patent
Yoshida et al.

(10) Patent No.: US 9,898,574 B2
(45) Date of Patent: Feb. 20, 2018

(54) METHOD FOR DETERMINING THE PRESENCE OF DISEASE

(71) Applicant: Sysmex Corporation, Kobe (JP)

(72) Inventors: Yuichiro Yoshida, Kobe (JP); Masaki Kobayashi, Kobe (JP); Yasuhiro Otomo, Kobe (JP)

(73) Assignee: Sysmex Corporation, Kobe, Hyogo (JP)

( * ) Notice: Subject to any disclaimer, the term of this patent is extended or adjusted under 35 U.S.C. 154(b) by 259 days.

(21) Appl. No.: 14/298,386

(22) Filed: Jun. 6, 2014

(65) Prior Publication Data

US 2014/0287965 A1    Sep. 25, 2014

Related U.S. Application Data

(62) Division of application No. 12/915,981, filed on Oct. 29, 2010, now abandoned.

(30) Foreign Application Priority Data

Oct. 30, 2009 (JP) ................................. 2009-251017

(51) Int. Cl.
   *G01N 33/48* (2006.01)
   *G06F 19/20* (2011.01)
   *G06F 19/24* (2011.01)
   *G06F 19/00* (2018.01)

(52) U.S. Cl.
   CPC .............. *G06F 19/20* (2013.01); *G06F 19/24* (2013.01); *G06F 19/3431* (2013.01)

(58) Field of Classification Search
   CPC ...................................... G06F 19/20
   USPC ........................................... 702/19
   See application file for complete search history.

(56) References Cited

U.S. PATENT DOCUMENTS

| 2007/0015183 A1 | 1/2007 | Krainc |
| 2008/0280774 A1 | 11/2008 | Burczynski et al. |
| 2009/0297494 A1 | 12/2009 | Cuenod et al. |
| 2011/0257888 A1 | 10/2011 | Otomo et al. |

FOREIGN PATENT DOCUMENTS

| CN | 101156067 A | 4/2008 |
| JP | 2005-323573 A | 11/2005 |
| WO | 02/059367 A2 | 8/2002 |
| WO | 03/083140 A2 | 10/2003 |
| WO | 2006/091254 A1 | 8/2006 |

OTHER PUBLICATIONS

Mamtani, Manju R. et al., "A simple method to combine multiple molecular biomarkers for dichotomous diagnostic classification", BMC Bioinformatics, BioMed Central, Oct. 10, 2006, vol. 7:442 pp. 1-12.
Chinese Office Action dated Oct. 19, 2012 in Chinese Patent Application No. 2012101600724700.

*Primary Examiner* — Jerry Lin
(74) *Attorney, Agent, or Firm* — Sughrue Mion, PLLC

(57) ABSTRACT

The invention provides a method for determining presence of a disease, comprising steps of; measuring the levels of expression of transcription products of genes in a biological sample obtained from a subject suspected of having a target disease, wherein the genes comprise at least one gene belonging to each of at least two disease-determining gene families related to the target disease; obtaining values representing deviations by standardizing the levels of the expression based on the levels of expression of transcription products of the corresponding genes in a plurality of healthy subjects; obtaining the average of values representing deviations with respect to the gene belonging to each of the disease-determining gene families; and determining whether or not the subject has the target disease by using the average; as well as a computer program product for determining presence of a disease.

20 Claims, 16 Drawing Sheets

FIG. 6A

|  | DETERMINATION METHOD OF INVENTION ||
|---|---|---|
|  | + | − |
| CROHN'S DISEASE PATIENTS 1 | 27 | 2 |
| HEALTHY SUBJECTS 1 | 2 | 19 |

SENSITIVITY 93.1%
SPECIFICITY 90.5%
CONCORDANCE RATE 92.0%

FIG. 6B

|  | DETERMINATION METHOD OF INVENTION ||
|---|---|---|
|  | + | − |
| CROHN'S DISEASE PATIENTS 2 | 29 | 1 |
| HEALTHY SUBJECTS 2 | 2 | 19 |

SENSITIVITY 96.7%
SPECIFICITY 90.5%
CONCORDANCE RATE 94.1%

FIG. 7A

|  | CONVENTIONAL DETERMINATION METHOD ||
|---|---|---|
|  | + | − |
| CROHN'S DISEASE PATIENTS 1 | 29 | 0 |
| HEALTHY SUBJECTS 1 | 0 | 21 |

SENSITIVITY 100%
SPECIFICITY 100%
CONCORDANCE RATE 100%

FIG. 7B

|  | CONVENTIONAL DETERMINATION METHOD ||
|---|---|---|
|  | + | − |
| CROHN'S DISEASE PATIENTS 2 | 28 | 2 |
| HEALTHY SUBJECTS 2 | 8 | 14 |

SENSITIVITY 93.3%
SPECIFICITY 63.6%
CONCORDANCE RATE 80.8%

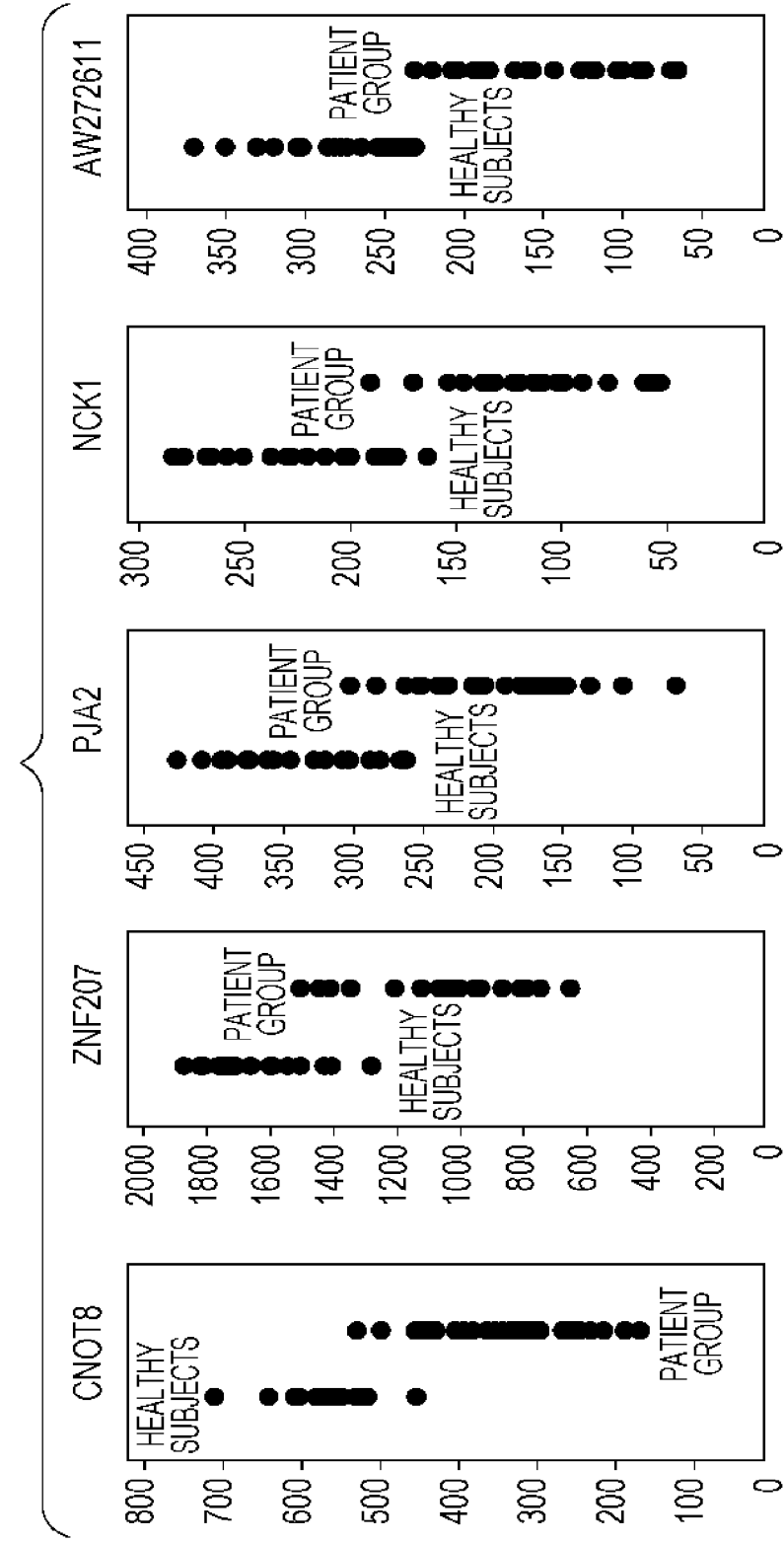

FIG. 9A

|  | CONVENTIONAL DETERMINATION METHOD | |
|---|---|---|
|  | + | − |
| CROHN'S DISEASE PATIENTS 1 | 28 | 1 |
| HEALTHY SUBJECTS 1 | 1 | 20 |

SENSITIVITY 96.6%
SPECIFICITY 95.2%
CONCORDANCE RATE 96.0%

FIG. 9B

|  | CONVENTIONAL DETERMINATION METHOD | |
|---|---|---|
|  | + | − |
| CROHN'S DISEASE PATIENTS 2 | 28 | 2 |
| HEALTHY SUBJECTS 2 | 13 | 8 |

SENSITIVITY 93.3%
SPECIFICITY 38.1%
CONCORDANCE RATE 70.1%

FIG. 11A

|  | DETERMINATION METHOD OF INVENTION ||
|---|---|---|
|  | + | − |
| HUNTINGTON'S DISEASE PATIENTS 1 | 6 | 0 |
| HEALTHY SUBJECTS 3 | 0 | 7 |

SENSITIVITY 100%
SPECIFICITY 100%
CONCORDANCE RATE 100%

FIG. 11B

|  | DETERMINATION METHOD OF INVENTION ||
|---|---|---|
|  | + | − |
| HUNTINGTON'S DISEASE PATIENTS 2 | 5 | 1 |
| HEALTHY SUBJECTS 4 | 0 | 7 |

SENSITIVITY 83.3%
SPECIFICITY 100%
CONCORDANCE RATE 92.3%

FIG. 12A

|  | CONVENTIONAL DETERMINATION METHOD ||
|---|---|---|
|  | + | − |
| HUNTINGTON'S DISEASE PATIENTS 1 | 6 | 0 |
| HEALTHY SUBJECTS 3 | 0 | 7 |

SENSITIVITY 100%
SPECIFICITY 100%
CONCORDANCE RATE 100%

FIG. 12B

|  | CONVENTIONAL DETERMINATION METHOD ||
|---|---|---|
|  | + | − |
| HUNTINGTON'S DISEASE PATIENTS 2 | 4 | 2 |
| HEALTHY SUBJECTS 4 | 0 | 7 |

SENSITIVITY 66.7%
SPECIFICITY 100%
CONCORDANCE RATE 84.6%

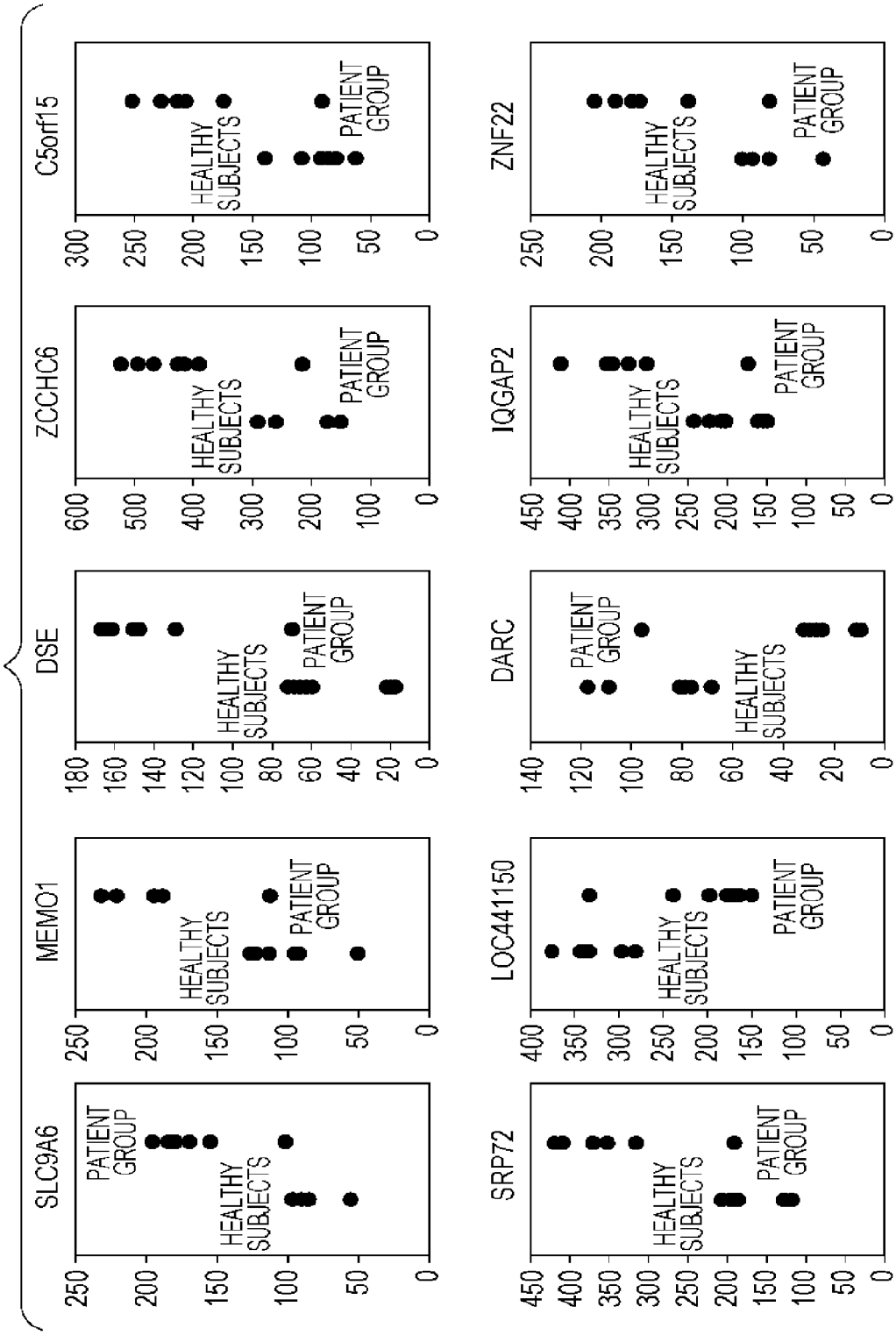

FIG. 14A

| | CONVENTIONAL DETERMINATION METHOD ||
|---|---|---|
| | + | − |
| HUNTINGTON'S DISEASE PATIENTS 1 | 6 | 0 |
| HEALTHY SUBJECTS 3 | 0 | 7 |

SENSITIVITY 100%
SPECIFICITY 100%
CONCORDANCE RATE 100%

FIG. 14B

| | CONVENTIONAL DETERMINATION METHOD ||
|---|---|---|
| | + | − |
| HUNTINGTON'S DISEASE PATIENTS 2 | 3 | 3 |
| HEALTHY SUBJECTS 4 | 0 | 7 |

SENSITIVITY 50.0%
SPECIFICITY 100%
CONCORDANCE RATE 76.9%

FIG. 16A

| | DETERMINATION METHOD OF INVENTION | |
|---|---|---|
| | + | − |
| LESION TISSUES 1 | 8 | 1 |
| NORMAL TISSUES 1 | 0 | 8 |

SENSITIVITY 88.9%
SPECIFICITY 100%
CONCORDANCE RATE 94.2%

FIG. 16B

| | DETERMINATION METHOD OF INVENTION | |
|---|---|---|
| | + | − |
| LESION TISSUES 2 | 6 | 2 |
| NORMAL TISSUES 2 | 1 | 7 |

SENSITIVITY 75.0%
SPECIFICITY 87.5%
CONCORDANCE RATE 81.3%

FIG. 17A

| | CONVENTIONAL DETERMINATION METHOD | |
|---|---|---|
| | + | − |
| LESION TISSUES 1 | 9 | 0 |
| NORMAL TISSUES 1 | 0 | 8 |

SENSITIVITY 100%
SPECIFICITY 100%
CONCORDANCE RATE 100%

FIG. 17B

| | CONVENTIONAL DETERMINATION METHOD | |
|---|---|---|
| | + | − |
| LESION TISSUES 2 | 5 | 3 |
| NORMAL TISSUES 2 | 0 | 8 |

SENSITIVITY 62.5%
SPECIFICITY 100%
CONCORDANCE RATE 81.3%

FIG. 19A

| | CONVENTIONAL DETERMINATION METHOD | |
|---|---|---|
| | + | − |
| LESION TISSUES 1 | 9 | 0 |
| NORMAL TISSUES 1 | 0 | 8 |

SENSITIVITY 100%
SPECIFICITY 100%
CONCORDANCE RATE 100%

FIG. 19B

| | CONVENTIONAL DETERMINATION METHOD | |
|---|---|---|
| | + | − |
| LESION TISSUES 2 | 0 | 8 |
| NORMAL TISSUES 2 | 0 | 8 |

SENSITIVITY 0%
SPECIFICITY 100%
CONCORDANCE RATE 50.0%

METHOD FOR DETERMINING THE PRESENCE OF DISEASE

CROSS REFERENCE TO RELATED APPLICATIONS

This is a Divisional Application of U.S. Application Ser. No. 12/915,981, filed Oct. 29, 2010, which claims priority based on Japanese Application No. 2009-251017 filed Oct. 30, 2009. The disclosures of the prior applications are incorporated herein by reference in their entirety.

FIELD OF THE INVENTION

The invention relates to a method for determining whether or not a subject has a target disease. More specifically, the invention relates to a method capable of determining whether or not a subject has a target disease, based on the measured levels of expression of transcription products of certain genes in a biological sample collected from the subject.

BACKGROUND

Exhaustive analysis of the levels of expression of a large number of genes or transcription products thereof makes it possible to find genes whose expression levels change in relation to certain diseases, and therefore has been expected to be applicable to determining the presence of such diseases. Therefore, many studies have been carried out on methods of determining whether or not a subject has a certain disease based on such exhaustive analysis data.

However, exhaustive analysis of the levels of expression of genes or transcription products thereof has a problem in which detection of a large number of false-positive genes, error in the measurement system, or poor reproducibility of gene expression makes it difficult to extract genes that show a truly significant change in expression level.

To solve such a problem, various statistical techniques for analytical data have been studied and developed.

For example, Japanese Patent Application Laid-Open (JP-A) No. 2005-323573 discloses a method of determining whether there is a significant difference in gene expression between two different conditions by multivariate analysis of data on gene expression levels obtained from a DNA microarray.

U.S. Patent Application Publication No. 2009/0297494 discloses a method of diagnosing mental disorders based on the levels of expression of genes involved in regulation of intracellular glutathione level.

SUMMARY OF THE INVENTION

The scope of the present invention is defined solely by the appended claims, and is not affected to any degree by the statements within this summary.

The method and computer program of the invention make it possible to conveniently determine whether or not a subject suspected of having a target disease has the target disease, using a biological sample from the subject. The invention also can provide objective means for determining whether or not a subject has the target disease. The invention also makes it possible to stably provide an accurate index to aid target disease diagnosis as compared with conventional methods.

BRIEF DESCRIPTION OF THE DRAWINGS

FIG. 6A shows the result of determination using averages of z-scores calculated from data on the levels of expression of gene transcription products in healthy subjects and Crohn's disease patients with respect to each of Crohn's disease-determining gene families, wherein the data are the same as those used in the identification of the gene families;

FIG. 6B shows the result of determination using averages of z-scores calculated from data on the levels of expression of gene transcription products in healthy subjects and Crohn's disease patients with respect to each of Crohn's disease-determining gene families, wherein the data differ from those used in the identification of the gene families;

FIG. 7A shows the result of determination using data on the levels of expression of gene transcription products in healthy subjects and Crohn's disease patients with respect to genes belonging to Crohn's disease-determining gene families, wherein the data are the same as those used in the identification of the gene families;

FIG. 7B shows the result of determination using data on the levels of expression of gene transcription products in healthy subjects and Crohn's disease patients with respect to genes belonging to Crohn's disease-determining gene families, wherein the data differ from those used in the identification of the gene families;

FIG. 8 shows the distributions of the levels of expression of genes which are identified as having a significant difference between healthy subjects and Crohn's disease patients from data on the levels of expression of gene transcription products in healthy subjects and Crohn's disease patients, which are the same as those used in the identification of Crohn's disease-determining gene families;

FIG. 9A shows the result of determination using data on the levels of expression of gene transcription products in healthy subjects and Crohn's disease patients with respect to genes having a significant difference between healthy subjects and Crohn's disease patients, wherein the data are the same as those used in the identification of Crohn's disease-determining gene families;

FIG. 9B shows the result of determination using data on the levels of expression of gene transcription products in healthy subjects and Crohn's disease patients with respect to genes having a significant difference between healthy subjects and Crohn's disease patients, wherein the data differ from those used in the identification of Crohn's disease-determining gene families;

FIG. 11A shows the result of determination using averages of z-scores calculated from data on the levels of expression of gene transcription products in healthy subjects and Huntington's disease patients with respect to each of Huntington's disease-determining gene families, wherein the data are the same as those used in the identification of the gene families;

FIG. 11B shows the result of determination using averages of z-scores calculated from data on the levels of expression of gene transcription products in healthy subjects and Huntington's disease patients with respect to each of Huntington's disease-determining gene families, wherein the data differ from those used in the identification of the gene families;

FIG. 12A shows the result of determination using data on the levels of expression of gene transcription products in healthy subjects and Huntington's disease patients with respect to genes belonging to Huntington's disease-determining gene families, wherein the data are the same as those used in the identification of the gene families;

FIG. 12B shows the result of determination using data on the levels of expression of gene transcription products in healthy subjects and Huntington's disease patients with respect to genes belonging to Huntington's disease-determining gene families, wherein the data differ from those used in the identification of the gene families;

FIG. 13 shows the distributions of the levels of expression of genes which are identified as having a significant difference between healthy subjects and Huntington's disease patients from data on the levels of expression of gene transcription products in healthy subjects and Huntington's disease patients, which are the same as those used in the identification of Huntington's disease-determining gene families;

FIG. 14A shows the result of determination using data on the levels of expression of gene transcription products in healthy subjects and Huntington's disease patients with respect to genes having a significant difference between healthy subjects and Huntington's disease patients, wherein the data are the same as those used in the identification of Huntington's disease-determining gene families;

FIG. 14B shows the result of determination using data on the levels of expression of gene transcription products in healthy subjects and Huntington's disease patients with respect to genes having a significant difference between healthy subjects and Huntington's disease patients, wherein the data differ from those used in the identification of Huntington's disease-determining gene families;

FIG. 16A shows the result of determination using averages of z-scores calculated from data on the levels of expression of gene transcription products in normal tissues and endometriosis lesion tissues with respect to each of endometriosis-determining gene families, wherein the data are the same as those used in the identification of the gene families;

FIG. 16B shows the result of determination using averages of z-scores calculated from data on the levels of expression of gene transcription products in normal tissues and endometriosis lesion tissues with respect to each of endometriosis-determining gene families, wherein the data differ from those used in the identification of the gene families;

FIG. 17A shows the result of determination using data on the levels of expression of gene transcription products in normal tissues and endometriosis lesion tissues with respect to genes belonging to endometriosis-determining gene families, wherein the data are the same as those used in the identification of the gene families;

FIG. 17B shows the result of determination using data on the levels of expression of gene transcription products in normal tissues and endometriosis lesion tissues with respect to genes belonging to endometriosis-determining gene families, wherein the data differ from those used in the identification of the gene families;

FIG. 19A shows the result of determination using data on the levels of expression of gene transcription products in normal tissues and endometriosis lesion tissues with respect to genes having a significant difference between normal tissues and endometriosis lesion tissues, wherein the data are the same as those used in the identification of endometriosis-determining gene families; and FIG. 19B shows the result of determination using data on the levels of expression of gene transcription products in normal tissues and endometriosis lesion tissues with respect to genes having a significant difference between normal tissues and endometriosis lesion tissues, wherein the data differ from those used in the identification of endometriosis-determining gene families.

DETAILED DESCRIPTION OF THE PREFERRED EMBODIMENTS

Figure 1:
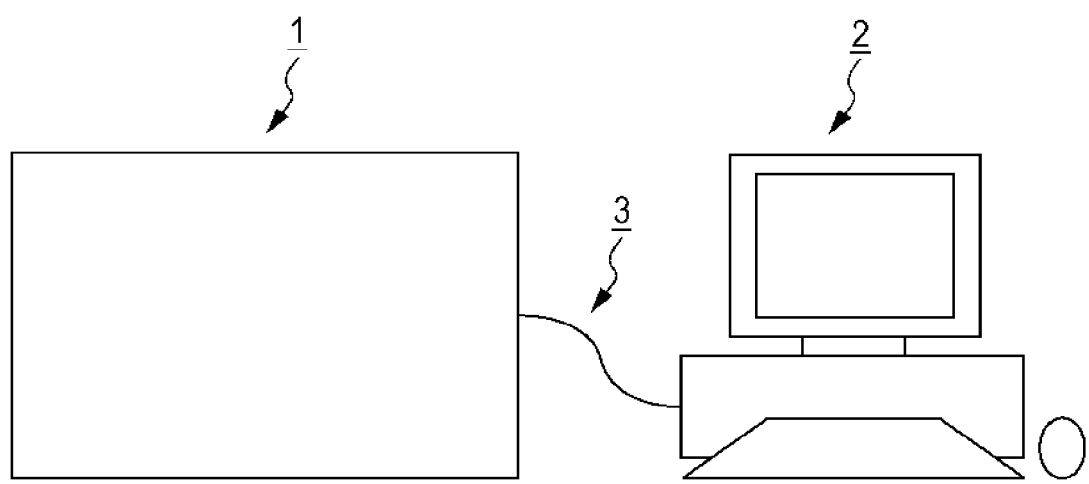
FIG. 1 is a diagram showing an example of an apparatus for determining the presence of a target disease, which is operated using the program of the invention.

Preferred embodiments of the invention are described below with reference to the drawings.

The determination method of the invention first measures the levels of expression of transcription products of genes in a biological sample obtained from a subject suspected of having a target disease, wherein the genes comprise at least one gene belonging to each of at least two disease-determining gene families related to the target disease.

The disease to be determined by the method of the invention (target disease) may be typically, but not limited to, a disease whose diagnosis has required advanced medical equipment such as CT or MRI scanner or a disease which lacks a specific symptom or a specific appearance and therefore is generally diagnosed by exclusion. Examples of such a disease include cancers (e.g., lung cancer, breast cancer, stomach cancer, colon cancer, cervical cancer, and melanoma), autoimmune diseases (e.g., rheumatism, systemic lupus erythematosus, Sjoegren syndrome, Guillain-Barre syndrome, and ulcerative colitis), infectious diseases (e.g., malaria, Japanese encephalitis, cholera, typhoid, and dysentery), psychiatric diseases or nervous system diseases (e.g., schizophrenia, bipolar disorder, Alzheimer's disease, and Huntington's disease), and diseases of unknown origin (e.g., Crohn's disease and endometriosis).

As used herein, the term "subject suspected of having a target disease" (hereinafter also simply referred to as "subject") means a subject that potentially has a target disease such as that described above and is to be determined to have or not to have the disease by the determination method of the invention.

The biological sample may be any sample which can be collected from an organism and from which transcription products of genes can be extracted. The blood (including whole blood, plasma, or serum), saliva, urine, hair, or the like of the subject may be used as the biological sample.

As used herein, the term "disease-determining gene families related to the target disease" means gene families whose relationship with the target disease is medically, biologically, or statistically clear. As long as such relationship is clear, any disease-determining gene families may be used in the determination method of the invention. In the determination method of the invention, gene families identified by the procedure described below may be used as the disease-determining gene families related to the target disease.

As used herein, the term "transcription products of genes" refers to products obtained by the transcription of the genes, which are intended to include ribonucleic acid (RNA), specifically, messenger RNA (mRNA).

As used herein, the term "the levels of expression of transcription products of genes" refers to the amounts of gene transcription products in the biological sample or the amounts of substances that reflect the amounts of the gene transcription products in the biological sample. Therefore, the determination method of the invention may measure the amounts of gene transcription products (mRNAs) or the amounts of complementary deoxyribonucleic acids (cDNAs) or complementary ribonucleic acids (cRNAs) derived from mRNAs. In general, the amount of mRNA in a biological sample is very small. Therefore, the amount of cDNA or cRNA derived therefrom by reverse transcription or in vitro transcription (IVT) is preferably measured.

The gene transcription products may be extracted from the biological sample by an RNA extraction method known in the art. For example, an RNA extract may be obtained by a process including centrifuging the biological sample to precipitate RNA-containing cells, physically or enzymatically destroying the cells, and removing the cell debris. The RNA extraction may also be performed using a commercially available RNA extraction kit or the like.

A treatment for removing a contaminant from the gene transcription product extract obtained as described above may also be performed. Such a contaminant, which is typically globin mRNA when the biological sample is blood, is derived from the biological sample and preferably absent in the measurement of the levels of expression of the gene transcription products.

The resulting gene transcription product extract is measured for the levels of expression of transcription products of genes comprising at least one gene belonging to each of at least two disease-determining gene families whose relationship with the target disease is known.

While the levels of expression of the gene transcription products may be measured by any known methods, they are preferably measured by quantitative PCR methods or methods using a nucleic acid chip, so that expression of transcription products of a large number of genes can be analyzed.

When the levels of expression of the gene transcription products are measured using a nucleic acid chip, a typical process may include: bringing cDNAs or cRNAs, which are prepared from the gene transcription product extract or the gene transcription products, into contact with about 20 to 25 mer nucleic acid probes fixed on a substrate; and measuring the change in fluorescence, coloring, current, or any other index to determine the presence or absence of hybridization, so that the levels of expression of the target gene transcription products can be determined.

At least one nucleic acid probe may be used for one gene transcription product, and two or more probes may be used depending on the length of the gene transcription product. The probe sequence may be appropriately determined by a person skilled in the art according to the sequence of the gene transcription product to be measured.

For example, GeneChip System available from Affymetrix, Inc. may be used in the method of measuring the levels of expression of the gene transcription products using a nucleic acid chip.

When a nucleic acid chip is used, the gene transcription products or cDNAs or cRNAs thereof may be fragmented so that the hybridization with the nucleic acid probes can be facilitated. The fragmentation may be performed by methods known in the art, such as methods using nuclease such as ribonuclease or deoxyribonuclease.

The amounts of the gene transcription products or cDNAs or cRNAs thereof to be in contact with the nucleic acid probes on the nucleic acid chip may generally be from about 5 to about 20 µg. The contact conditions are generally 45° C. for about 16 hours.

Whether or not and how much the gene transcription products or cDNAs or cRNAs thereof hybridize with the nucleic acid probes can be detected using a fluorescent substance or a dye or based on a hybridization-induced change in the amount of current flowing on the nucleic acid chip.

When the hybridization is measured by the detection of a fluorescent substance or a dye, the gene transcription products or cDNAs or cRNAs thereof are preferably labeled with a marker for the detection of the fluorescent substance or the dye. Such a marker may be one generally used in the art. In general, biotinylated nucleotide or biotinylated ribonucleotide may be mixed as a nucleotide or ribonucleotide substrate in the synthesis of cDNAs or cRNAs so that biotin-labeled cDNAs or cRNAs can be obtained. The biotin-labeled cDNAs or cRNAs can be coupled to avidin or streptavidin, which is a binding partner to biotin, on the nucleic acid chip. The binding of avidin or streptavidin to an appropriate fluorescent substance or dye makes it possible to detect the hybridization. Examples of the fluorescent substance include fluorescein isothiocyanate (FITC), green-fluorescent protein (GFP), luciferin, and phycoerythrin. In general, a phycoerythrin-streptavidin conjugate is commercially available and therefore conveniently used.

Alternatively, a labeled antibody to avidin or streptavidin may also be brought into contact with avidin or streptavidin so that the fluorescent substance or dye of the labeled antibody can be detected.

The levels of expression of the gene transcription products obtained in this step may be any type of values that can relatively indicate the amount of each gene transcription product in the biological sample. When the measurement is performed using the nucleic acid chip, the levels of expression may be signals obtained from the nucleic acid chip, which are based on the intensity of fluorescence, the intensity of coloring, the amount of current, or the like.

Such signals may be measured using a nucleic acid chip analyzer.

The measured levels of expression are then standardized based on the levels of expression of transcription products of the corresponding genes in a plurality of healthy subjects so that values representing deviations are obtained.

As used herein, the term "transcription products of the corresponding genes" means transcription products of the same genes as those whose expression levels in the subject are measured.

The levels of expression of transcription products of the corresponding genes in a plurality of healthy subjects may be obtained by a process including: collecting biological samples from healthy subjects by the same method as that is performed to collect the biological sample from the subject; and measuring the levels of expression of transcription products of the object genes using the biological samples.

As used herein, the term "healthy subject" refers to a subject that can be confirmed not to have the target disease, based on criteria other than those for the determination method of the invention. For example, the healthy subject may be a subject that can be confirmed not to have cancer (as the target disease) by tissue characterization, CT, MRI, tumor marker method, or the like, an autoimmune disease (ditto) by blood test or the like, an infectious disease (ditto) by blood test or the like, a psychiatric disease or a nervous system disease (ditto) by diagnostic brain imaging, genetic testing, inquiry, interview sheet method, or the like, Crohn's disease (ditto) by endoscopy, digestive tract imaging, or the like, or endometriosis (ditto) by CT, MRI, endoscopy, or the like.

As used herein, the term "a plurality of healthy subjects" means a statistically sufficient number of healthy subjects, which may be 30 or more, preferably 40 or more healthy subjects.

As used herein, the phrase "standardizing (or standardized) based on the levels of expression of transcription products of the corresponding genes in a plurality of healthy subjects" means that values representing deviations are calculated from the following formula: a value representing a deviation={(the level of expression of a transcription product of a gene in a subject)−(the average of the levels of expression of the transcription product of the corresponding gene in a plurality of healthy subjects)}/(the standard deviation of the levels of expression of the transcription product of the corresponding gene in the plurality of healthy subjects).

The value representing a deviation is also known as a z-score, which indicates how much the level of expression of the transcription product of the gene in the subject deviates from the level of expression of the transcription product of the gene in the plurality of healthy subjects.

Alternatively, in the determination method of the invention, the level of expression of a transcription product of a gene in a subject may be divided by the average of the levels of expression of the transcription product of the corresponding gene in a plurality of healthy subjects in order to obtain the ratio of the expression level in the subject to the expression level in the healthy subjects, and the next step may be performed using the value representing the expression level ratio in place of the value representing a deviation.

The value representing the expression level ratio indicates how much the level of expression of the transcription product of the gene in the subject is larger than the average of the levels of expression of the transcription product of the corresponding gene in the plurality of healthy subjects.

Subsequently, the average of values representing deviations with respect to the gene belonging to each of the selected disease-determining gene families is obtained.

When a value representing a deviation is obtained for only one gene belonging to the gene family for which an average is to be obtained, the term "average" as used herein means a value representing a deviation for the one gene, and when values representing deviations are obtained for two or more genes, the term "average" as used herein means the average of these values representing deviations.

The average is obtained for at least two gene families selected from disease-determining gene families whose relationship with the target disease is known. The number of the selected gene families is preferably as large as possible.

Whether or not the subject has the target disease is determined using the average obtained as described above.

The determination may be made by inputting the average obtained as described above from the subject to a determination formula, which is obtained based on: averages previously obtained in the same manner as in the respective steps described above using biological samples collected from healthy subjects; and averages previously obtained in the same manner as in the respective steps described above using biological samples collected from patients having the target disease.

The determination formula may be prepared using discriminant analysis methods known per se. Discriminant analysis methods are statistical methods which can provide criteria for determining which of two different groups newly obtained data belongs to, provided that previously presented pieces of data are known to be classified into the two different groups. Examples of such discriminant analysis methods include a support vector machine (SVM), a linear discriminant analysis, a neural network, a k-neighborhood discriminator, a decision tree, a random forest, and so on. Among these discriminant analysis methods, a SVM, which is also installed on statistical analysis software GeneSpring, is preferably used in the preparation of the determination formula.

The averages obtained from the healthy subjects and the averages obtained from the target disease patients may be previously input so that a determination formula can be prepared using a SVM. The average determined from the biological sample collected from the subject may be input to the SVM with which the determination formula is prepared, so that it can be determined whether or not the subject has the target disease.

As described above, the determination method of the invention is performed using "disease-determining gene families related to the target disease." For example, such gene families may be gene families statistically related to the target disease. For example, the gene families statistically related to the target disease may be identified by a procedure including the following steps of:

(a) measuring the levels of expression of transcription products of genes in a biological sample obtained from each of a plurality of patients having the target disease and a plurality of healthy subjects;

(b) standardizing the levels of the expression in each of the plurality of patients based on the levels of expression of the transcription products of the corresponding genes in the plurality of healthy subjects to obtain values representing deviations for each of the plurality of patients;

standardizing the levels of the expression in each of the plurality of healthy subjects to obtain values representing deviations for each of the plurality of healthy subjects;

(c) classifying the genes, whose expression levels are measured, into at least two gene families using a classification system based on the function of molecules encoded by the genes;

obtaining, as an average for each gene family, the average of values representing deviations for the gene belonging to each of the gene families with respect to each of the plurality of patients and the plurality of healthy subjects;

(d) obtaining a significance probability between the average for each gene family with respect to the plurality of patients and the average for each corresponding gene family with respect to the plurality of healthy subjects; and (e) identifying the gene family as a disease-determining gene family related to the target disease, when the significance probability for the gene family is 0.05 or less.

The first step is to measure the levels of expression of gene transcription products in a biological sample obtained from each of a plurality of patients having the target disease and a plurality of healthy subjects.

As used herein, the term "patients having the target disease" (hereinafter also simply referred to as "patients") refers to subjects that can be confirmed to have the target disease based on criteria other than those for the determination method of the invention. For example, the patients are humans that can be confirmed to have cancer (as the target disease) by tissue characterization, CT, MRI, tumor marker method, or the like, an autoimmune disease (ditto) by blood test or the like, an infectious disease (ditto) by blood test or the like, a psychiatric disease or a nervous system disease (ditto) by diagnostic brain imaging, genetic testing, inquiry, or the like, Crohn's disease (ditto) by endoscopy, digestive tract imaging, or the like, or endometriosis (ditto) by CT, MRI, endoscopy, or the like.

As used herein, the term "a plurality of patients" means a statistically sufficient number of patients, which may be 30 or more, preferably 40 or more patients. The terms "healthy subject" and "a plurality of healthy subjects" have the same meanings as defined above.

This step may include extracting the gene transcription products and measuring the levels of expression of the transcription products, which may be performed in the same manner as in the respective steps of the above determination method of the invention using the biological sample obtained from each of the plurality of patients having the target disease and the plurality of healthy subjects.

The levels of the expression in each of the plurality of patients are standardized based on the levels of expression of the transcription products of the corresponding genes in the plurality of healthy subjects, so that values representing deviations for each of the plurality of patients are obtained.

As used herein, the phrase "the levels of the expression in each of the plurality of patients are standardized based on the levels of expression of the transcription products of the corresponding genes in the plurality of healthy subjects" means that values representing deviations for all of the plurality of patients are calculated from the following formula: a value representing a deviation for a patient={(the level of expression of a transcription product of a gene in each patient)−(the average of the levels of expression of the transcription product of the corresponding gene in a plurality of healthy subjects)}/(the standard deviation of the levels of expression of the transcription product of the corresponding gene in the plurality of healthy subjects).

The levels of the expression in each of the plurality of healthy subjects are also standardized so that values representing deviations for each of the plurality of healthy subjects are obtained.

In this case, "standardized (standardizing)" has the same meaning as commonly used in the field of statistics. Specifically, values representing deviations for all of the plurality of healthy subjects may be obtained using the following formula: a value representing a deviation for a healthy subject={(the level of expression of a transcription product of a gene in each healthy subject)−(the average of the levels of expression of the transcription product of the gene in a plurality of healthy subjects)}/(the standard deviation of the levels of expression of the transcription product of the gene in the plurality of healthy subjects).

The ratio of the expression level in each of the plurality of patients to the average for the healthy subjects and the ratio of the expression level in each of the healthy subjects to the average for the healthy subjects may be calculated in the same manner as in the calculation of the value representing the ratio of the expression level in the subject to the expression level in the healthy subjects, and these expression level ratios may be used in place of the value representing a deviation for each of the plurality of patients and the value representing a deviation for each of the healthy subjects.

Subsequently, the genes, whose expression levels are measured, are classified into at least two gene families using a classification system based on the function of molecules encoded by the genes, and the average of values representing deviations for the gene belonging to each of the gene families is obtained as an average for each gene family with respect to each of the plurality of patients and the plurality of healthy subjects.

As used herein, the term "classification system based on the function of molecules encoded by the genes" means a database in which genes are classified according to the function of molecules encoded by the genes. Known databases may be used, examples of which include Gene Ontology (GO), Kyoto Encyclopedia of Genes and Genomes (KEGG), MetaCyc, GenMAPP, BioCarta, KeyMolnet, and Online Mendelian Inheritance in Man (OMIM). In particular, Gene Ontology is preferably used, in which gene families are defined with terms called "GO Terms."

These databases are available from the URLs shown in Table 1 below.

TABLE 1

| | URL |
|---|---|
| GO | geneontology.org/index.shtml |
| KEGG | kegg.jp/kegg/brite.html |
| MetaCyc | metacyc.org/META/class-tree?object=Gene-Ontology-Terms |
| GenMAPP | genmapp.org/ |
| BioCarta | biocarta.com/genes/allPathways.asp |
| KeyMolnet | immd.co.jp/keymolnet/index.html |
| OMIM | ncbi.nlm.nih.gov/omim/ |

In this step, the genes, whose expression levels are measured, are first classified into at least two gene families using the classification system. The average for each classified gene family is then obtained with respect to each of the plurality of patients and the plurality of healthy subjects in the same manner as in the step of obtaining the average for the subject described above.

Subsequently, a significance probability is obtained between the average for each gene family with respect to the plurality of patients and the average for each corresponding gene family with respect to the plurality of healthy subjects.

As used herein, the term "corresponding gene family" means the same gene family as the gene family for which the average is obtained with respect to the plurality of patients.

A t-test may be used to determine the significance probability (hereinafter also referred to as "p-value") between the average for each gene family with respect to the plurality of patients and the average for each corresponding gene family with respect to the plurality of healthy subjects.

When the resulting p-value for the gene family is 0.05 or less, the gene family is identified as a disease-determining gene family related to the target disease.

In the determination method of the invention, at least two selected from the gene families identified by the above procedure are used as disease-determining gene families related to the target disease. The number of the selected disease-determining gene families is preferably as large as possible.

In the determination method of the invention, the levels of expression of the gene transcription products are not directly used, but values representing deviations are obtained from the expression levels and then used to determine the average for the disease-determining gene family, and the resulting average is used, so that a subject having the target disease can be clearly and stably distinguished from healthy subjects.

For example, the determination method of the invention is particularly suitable for use in determining the presence of such a disease as Crohn's disease, Huntington's disease, or endometriosis.

Crohn's disease is a disease of unknown etiology, which has a granulomatous, inflammatory lesion associated with an ulcer or fibrosis and can affect the whole of the digestive tract from the oral cavity to the anus. Now, at least 20,000 people in Japan suffer from this disease. Common symptoms of this disease include stomachache, diarrhea, weight loss, fever, and anal lesion. While confirmed diagnosis of Crohn's disease is performed by endoscopy, it is believed that early detection of this disease can be achieved by screening test using a less invasive test such as blood test. The determination method of the invention may be performed on a subject suspected of having Crohn's disease, so that a reliable determination result can be obtained as an index of diagnosis.

When the determination method of the invention is used to determine the presence of Crohn's disease, examples of the disease-determining gene family include a G protein-related gene family, a blood coagulation-related gene family, an oxidative stress-related gene family, a phagocytosis-related gene family, and a fat oxidation-related gene family.

According to the GO Terms, the above five gene families are categorized as "heterotrimeric G-protein complex" (GO: 0005834), "blood coagulation" (GO:0007596), "response to oxidative stress" (GO:0006979), "phagocytosis, engulfment" (GO:0006911), and "fatty acid oxidation" (GO: 0019395), respectively.

Huntington's disease is a chronic progressive neurodegenerative disease whose main symptoms include involuntary movement (mainly choreic movement), mental manifestation, and dementia. When diagnosed, this disease must be discriminated from symptomatic chorea caused by cerebrovascular disorders such as cerebral bleeding, drug-induced chorea caused by antipsychotic drugs, and other diseases such as Wilson's disease. Therefore, the determination method of the invention may be performed on a subject suspected of having Huntington's disease, so that a reliable determination result can be obtained as an index of diagnosis.

When the determination method of the invention is used to determine the presence of Huntington's disease, examples of the disease-determining gene family include a microtubule-related gene family, a mitochondria-related gene family, and a prostaglandin-related gene family.

According to the GO terms, the three gene families are categorized as "microtube" (GO:0005874), "mitochondrion" (GO:0005739), and signal transduction (GO: 0007165), respectively.

Endometriosis is a disease in which endometria or endometrial-like tissues grow in the uterine cavity or outside the uterine body. Main symptoms of endometriosis are menstrual colic and dysmenorrhea. Therefore, endometriosis is difficult to be discriminated from dysmenorrhea. Thus, the determination method of the invention may be performed on a subject suspected of having endometriosis, so that a reliable determination result can be obtained as an index of diagnosis.

When the determination method of the invention is used to determine the presence of endometriosis, examples of the disease-determining gene family include a cytokine synthesis process-related gene family, a cytokine-mediated signaling-related gene family, and an immunoglobulin-mediated immune response-related gene family.

According to the GO terms, the three gene families are categorized as "cytokine biosynthetic process" (GO: 0042089), "cytokine-mediated signaling pathway" (GO: 0019221), and "immunoglobulin mediated immune response" (GO:0016064), respectively.

When the determination method of the invention is used, a patient with the target disease is preferably determined to be "positive" at a sensitivity of 80% or more, more preferably 85% or more, even more preferably 90% or more. When the determination method of the invention is used, a healthy subject is preferably determined to be "negative" at a specificity of 80% or more, more preferably 85% or more, even more preferably 90% or more.

The determination method of the invention, which shows such high sensitivity and specificity, can stably provide a high-accuracy index to aid in diagnosing the target disease.

Another embodiment of the invention is directed to a program that enables a computer to execute the method of the invention for determining the presence of a disease. Specifically, the program of the invention includes a program for determining the presence of a disease, which enables a computer to function as:

receiving means for receiving data on the levels of expression of transcription products of genes in a biological sample obtained from a subject suspected of having a target disease, wherein the genes comprise at least one gene belonging to each of at least two disease-determining gene families related to the target disease;

deviation obtaining means for obtaining values representing deviations by standardizing the levels of the expression based on the levels of expression of transcription products of the corresponding genes in a plurality of healthy subjects;

average obtaining means for obtaining the average of values representing deviations with respect to the gene belonging to each of the disease-determining gene families;

determination means for determining, using the average, whether or not the subject has the target disease; and output means for outputting the result of the determination by the determination means.

The program of the invention may also enable a computer to function as disease-determining genes-identifying means. Specifically, the program of the invention includes a program for determining the presence of a disease, which further enables a computer to function as:

receiving means for receiving the levels of expression of transcription products of genes in a biological sample obtained from each of a plurality of patients having the target disease and a plurality of healthy subjects;

deviation obtaining means for obtaining values representing deviations for each of the plurality of patients by standardizing the levels of the expression in each of the plurality of patients based on the levels of expression of the transcription products of the corresponding genes in the plurality of healthy subjects and for obtaining values representing deviations for each of the plurality of healthy subjects by standardizing the levels of the expression in each of the plurality of healthy subjects;

average obtaining means for classifying the genes, whose expression levels are measured, into at least two gene families using a classification system based on the function of molecules encoded by the genes and for obtaining, as an average for each gene family, the average of values representing deviations for the gene belonging to each of the gene families with respect to each of the plurality of patients and the plurality of healthy subjects;

significance probability obtaining means for obtaining a significance probability between the average for each gene family with respect to the plurality of patients and the average for each corresponding gene family with respect to the plurality of healthy subjects; and gene family identifying means for identifying the gene family as a disease-determining gene family related to the target disease when the significance probability for the gene family is 0.05 or less.

FIG. 1 shows an example of an apparatus for determining the presence of a target disease, in which the program of the invention is used. The apparatus includes a gene transcription product expression level-measuring device 1, a computer 2, and a cable 3 connecting them together. Data on the expression levels measured by the gene transcription product expression level-measuring device 1, such as signals based on the intensity of fluorescence, the amount of current, or the like can be sent to the computer 2 through the cable 3. Alternatively, the gene transcription product expression level-measuring device 1 may be unconnected with the computer 2. In this case, the expression level data may be input to the computer to run the program described above.

The computer 2 obtains the values representing deviations from the resulting expression levels, obtains the average of the resulting values representing deviations for each of at least two gene families, and determines whether or not the subject has the target disease based on the average.

Figure 2:
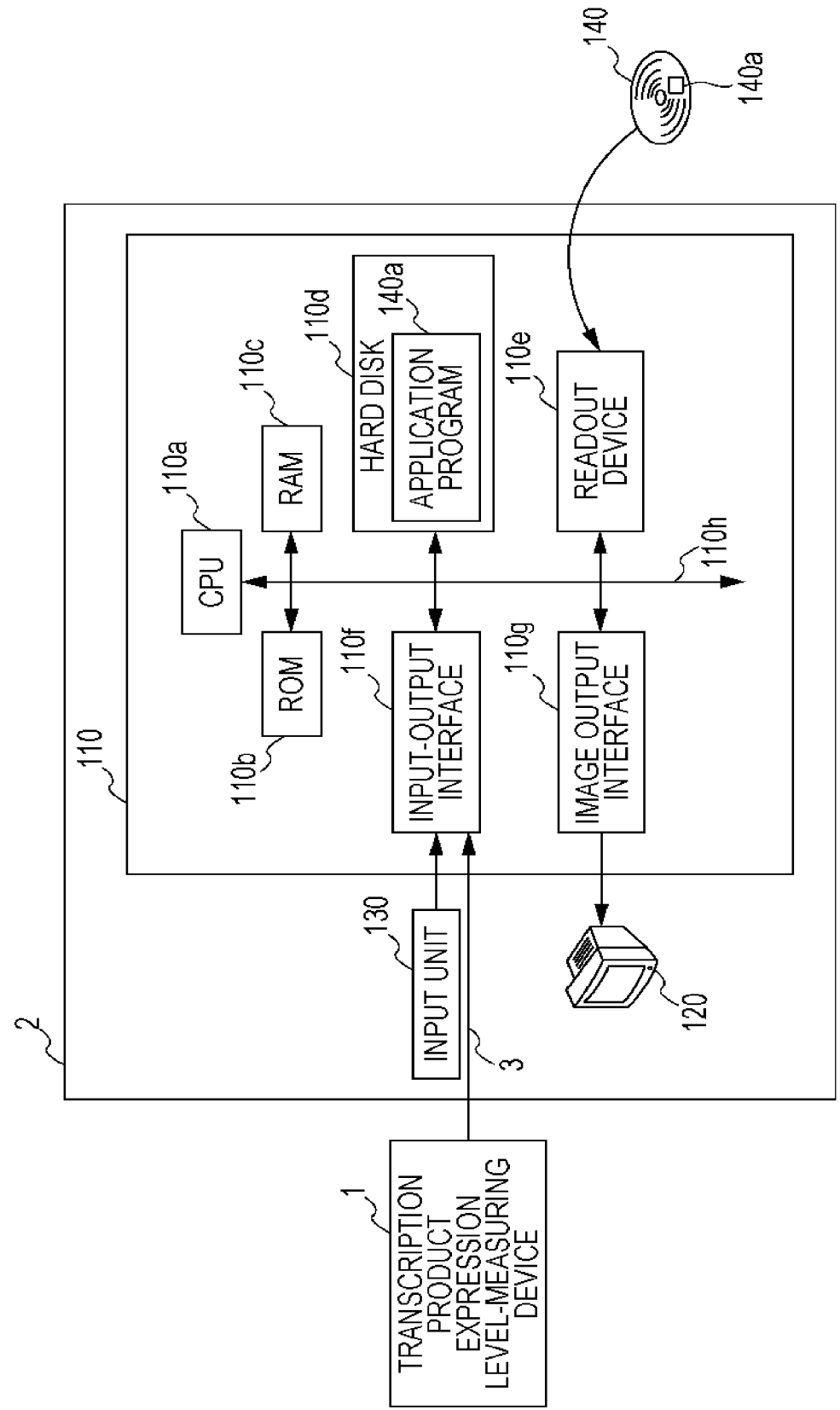
FIG. 2 is a diagram showing an example of a computer system that executes the program of the invention.

The determination method of the invention can be implemented by the program of the invention in cooperation with the computer 2 including a central processing unit, a storage unit, a reader for a recording medium such as a compact disc or a Floppy® disc, an input unit such as a keyboard, and an output unit such as a display. FIG. 2 shows a more specific example of the computer system for implementing the method.

The computer 2 shown in FIG. 2 mainly includes a main unit 110, a display 120, and an input unit 130. The main unit 110 mainly includes a CPU 110a, a ROM 110b, a RAM 110c, a hard disk 110d, a readout device 110e, an input-output interface 110f, and an image output interface 110g. The CPU 110a, ROM 110b, RAM 110c, hard disk 110d, readout device 110e, input-output interface 110f, and image output interface 110g are connected to one another through a bus 110h to allow data communication.

The CPU 110a can execute the computer program stored in the ROM 110b and the computer program loaded on the RAM 110c.

The ROM 110b includes a mask ROM, PROM, EPROM, EEPROM, or the like. The ROM 110b stores the computer program to be executed by the CPU 110a and the data to be used for the execution.

The RAM 110c includes an SRAM, DRAM or the like. The RAM 110c is used to read out the computer program stored in the RAM 110c, ROM 110b, and hard disk 110d. When these computer programs are executed, the RAM 110c is also used as a work area for the CPU 110a.

Various computer programs to be executed by the CPU 110a, such as an operating system and application programs, and data to be used for the execution of the computer program are stored on the hard disk 110d. In an embodiment of the invention, the data stored on the hard disk 110d also include data on the levels of expression of transcription products of the corresponding genes in a plurality of healthy subjects (hereinafter referred to as "stored expression level data"), data on disease-determining gene families (hereinafter referred to as "disease-determining gene family data"), and a determination formula for determining whether or not the subject has the target disease. The determination formula is obtained using the discriminant analysis method based on averages previously determined with biological samples collected from healthy subjects and averages previously determined with biological samples collected from patients having the target disease. An application program 140a as described below is also installed on the hard disk 110d.

The readout device 110e includes a flexible disk drive, a CD-ROM drive, or a DVD-ROM drive or the like and can read out the computer program or data stored on a transportable recording medium 140. An application program 140a that enables the computer to execute the method of this embodiment is also stored on the transportable recording medium 140. The CPU 110a can read out the application program 140a according to the invention from the transportable recording medium 140, and the application program 140a can be installed on the hard disk 110d.

The application program 140a may be provided not only from the transportable recording medium 140 but also from external equipment communicably connected to the main unit 110 of the computer through a telecommunication line (regardless of whether it is wire-line or wireless). For example, the application program 140a may be stored on the hard disk of a server computer on the Internet, and the CPU 110a may access the server computer to download the application program and install it on the hard disk 110d.

An operating system to provide a graphical user interface environment, such as Windows® manufactured and sold by Microsoft Corporation in the United States is installed on the hard disk 110d. A description will be given below, provided that the application program 140a according to this embodiment runs on the operating system.

For example, the input-output interface 110f includes a serial interface such as USB, IEEE 1394, or RS-232C, a parallel interface such as SCSI, IDE, or IEEE 1284, and an analog interface including a D/A converter, an A/D converter, or the like. The transcription product expression level-measuring device 1 is connected to the input-output interface 110f through the cable 3 so that the expression level data determined in the transcription product expression level-measuring device 1 can be input to the main unit 110 of the computer. The input unit 130 including a keyboard and a mouse is also connected to the input-output interface 110f so that the user can input data to the main unit 110 of the computer using the input unit 130.

The image output interface 110g is connected to the display 120 including an LCD, CRT, or the like so that an image signal corresponding to the image data sent from the CPU 110*a* can be output on the display 120. The display 120 outputs an image (on the screen) according to the image signal input.

Figure 3:
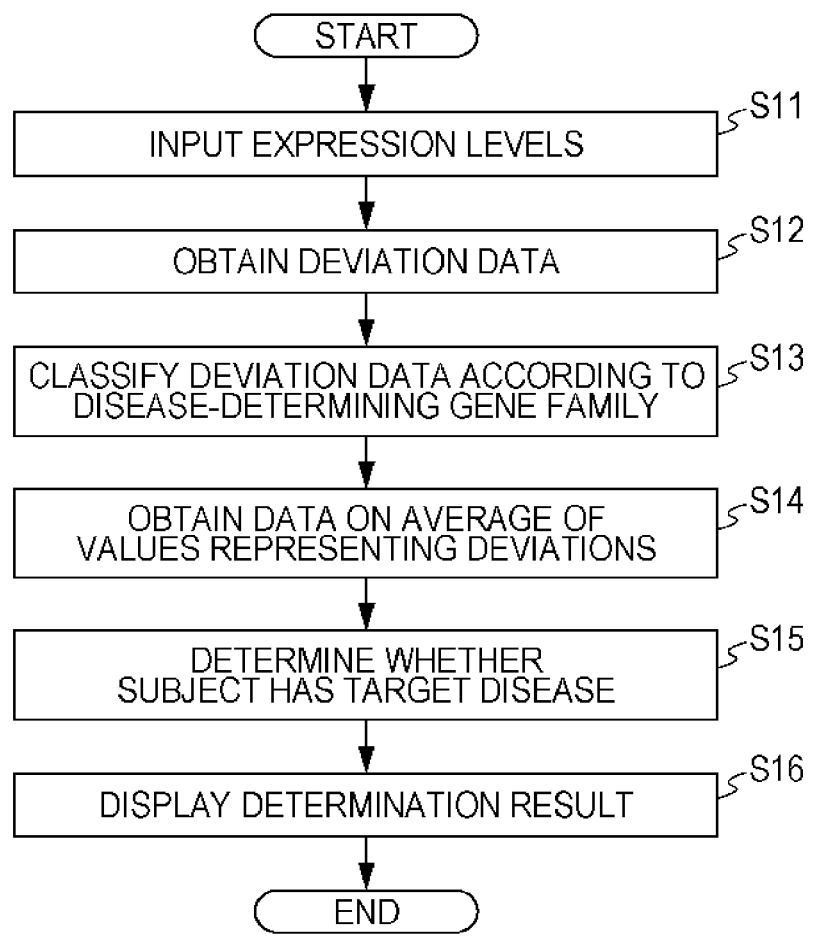
FIG. 3 is a flow chart showing a specific operation according to the program of the invention.

FIG. 3 is a flow chart more specifically showing how the program of the invention runs on the computer 2.

First, when the levels of expression of transcription products of genes are measured in the gene transcription product expression level-measuring device 1, the transcription product expression level-measuring device 1 outputs the data on the measured expression levels (hereinafter referred to as "measured expression level data") to the computer 2. The CPU 110*a* receives the output measured expression level data and stores the data into the RAM 110*c* (step S11).

Subsequently, the CPU 110*a* reads out the stored expression level data, which has previously been stored on the hard disk 110*d*, and obtains data showing values representing deviations (hereinafter referred to as "deviation data") based on the input measured expression level data and the stored expression level data (step S12).

Subsequently, the CPU 110*a* reads out the disease-determining gene family data, which has previously been stored on the hard disk 110*d*, and determines whether or not the genes for the deviation data belong to the disease-determining gene families, so that the deviation data obtained is classified according to disease-determining gene family (step S13).

Subsequently, the CPU 110*a* uses the deviation data classified according to disease-determining gene family to obtain data showing the average of values representing deviations for each of the disease-determining gene families (hereinafter referred to as "average data") (step S14).

Subsequently, the CPU 110*a* reads out the determination formula, which has previously been stored on the hard disk 110*d*, and applies the average data to the determination formula to determine whether or not the subject has the target disease (step S15).

Subsequently, the CPU 110*a* stores the result of determining whether or not the subject has the target disease into the RAM 110*c* and displays the result on the display 120 of the computer through the image output interface 110*g* (step S16).

While, in this embodiment, the CPU 110*a* obtains the measured expression level data from the transcription product expression level-measuring device 1 through the input-output interface 110*f*, any other configuration may also be used. For example, the levels of expression of gene transcription products may be determined in a transcription product expression level-measuring device independent of the computer 2, and the operator may use the input unit 130 to input the measured expression level data to the computer 2.

Figure 4:
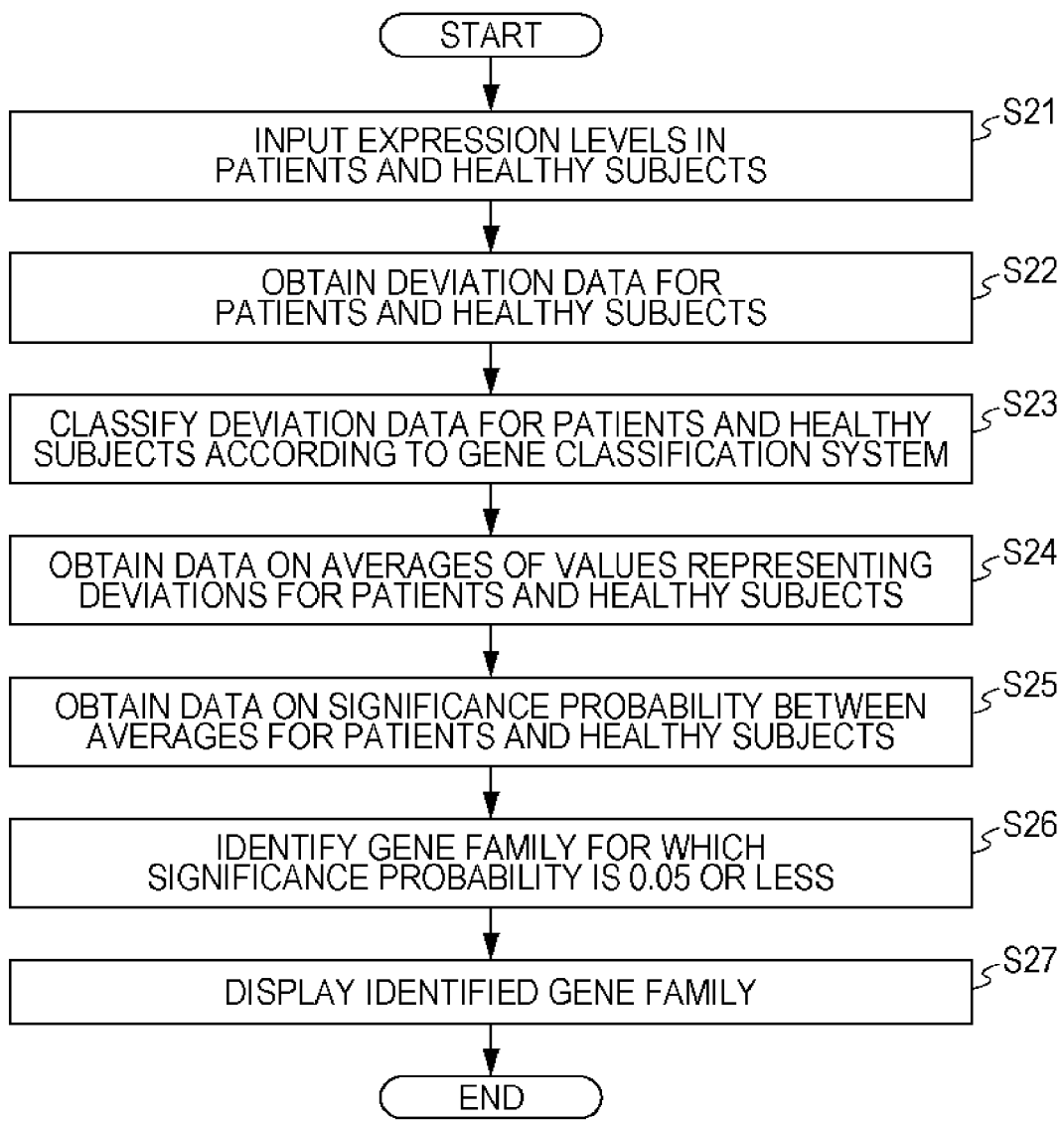
FIG. 4 is a flow chart showing a specific operation according to the program of the invention for identifying disease-determining gene families.

FIG. 4 is a flow chart specifically showing how the program of the invention runs on the computer to enable it to function as disease-determining gene-identifying means. In this embodiment, the hard disk 110*d* stores data on a classification system based on the function of molecules encoded by genes (hereinafter referred to as "classification system data").

First, when the levels of expression of transcription products of genes in a plurality of patients and a plurality of healthy subjects are measured in the gene transcription product expression level-measuring device 1, the transcription product expression level-measuring device 1 outputs, to the computer 2, data on the measured expression levels in the plurality of patients (hereinafter referred to as "measured patient expression level data") and data on the measured expression levels in the plurality of healthy subjects (hereinafter referred to as "measured healthy subject expression level data"). The CPU 110*a* receives the output measured patient expression level data and the output measured healthy subject expression level data, and stores the data into the RAM 110*c* (step S21).

Subsequently, the CPU 110*a* standardizes the measured patient expression level data for each of the plurality of patients based on the measured healthy subject expression level data on the transcription products of the corresponding genes in the plurality of healthy subjects, so that data showing values representing deviations are obtained for each of the plurality of patients (hereinafter referred to as "patient deviation data"), and the CPU 110*a* also standardizes the measured expression level data for each of the plurality of healthy subjects, so that data showing values representing deviations are obtained for each of the plurality of healthy subjects (hereinafter referred to as "healthy subject deviation data") (step S22).

Subsequently, the CPU 110*a* reads out the classification system data, which has previously been stored on the hard disk 110*d*, and classifies the patient deviation data according to gene family, based on the genes for the patient deviation data. The CPU 110*a* also classifies the healthy subject deviation data according to gene family, based on the genes for the healthy subject deviation data (step S23).

Subsequently, the CPU 110*a* uses the patient deviation data classified according to gene family to obtain data showing the average of values representing deviations for each of the gene families (hereinafter referred to as "patient average data"). The CPU 110*a* also uses the healthy subject deviation data classified according to gene family to obtain data showing the average of values representing deviations for each of the gene families (hereinafter referred to as "healthy subject average data") (step S24).

Subsequently, the CPU 110*a* uses the resulting patient average data and healthy subject average data for each gene family to obtain data showing the significance probability between the average for the plurality of patients and the average for the plurality of healthy subjects (hereinafter referred to as "significance probability data") (step S25).

Subsequently, the CPU 110*a* uses the resulting significance probability data to identify the gene family for which the significance probability is 0.05 or less (step S26).

Subsequently, the CPU 110*a* stores the identified gene family into the RAM 110*c* and displays it on the display 120 of the computer through the image output interface 110*g* (step S27).

While, in this embodiment, the CPU 110*a* obtains the measured patient expression level data and the measured healthy subject expression level data from the transcription product expression level-measuring device 1 through the input-output interface 110*f*, any other configuration may also be used. For example, the levels of expression of the gene transcription products in the plurality of patients and healthy subjects may be determined in a transcription product expression level-measuring device independent of the computer 2, and the operator may use the input unit 130 to input the measured patient expression level data and the measured healthy subject expression level data to the computer 2.

While, in this embodiment, the identified gene family is displayed on the display 120 in step S27, the data on the identified gene family may also only be stored as disease-determining gene family data into the RAM 110*c*. The stored disease-determining gene family data may also be used, for example, in the operation of the computer 2 shown in FIG. 2.

EXAMPLES

The invention is more specifically described in the examples below, which are not intended to limit the scope of the invention.

Example 1 (Method for Determining the Presence of Crohn's Disease)

(1) Identification of Crohn's Disease-Determining Gene Families

Data available from the Gene Expression Omnibus (GEO, ncbi.nlm.nih.gov/geo), which was a gene expression data bank, were used in Example 1, which were data on the levels of expression of gene transcription products in the blood of Crohn's disease patients and healthy subjects. The data were normalized data obtained by normalization of raw measured signal data, which are available from ncbi.nlm.nih.gov/sites/GDSbrowser?acc=GDS1615.

(1-1) Selection of Samples and Probe Sets

Data on Crohn's disease patients 1 (29 samples) and data on healthy subjects 1 (21 samples) were randomly selected from the data described above, and these data were used to identify Crohn's disease-determining gene families.

The data on Crohn's disease patients and healthy subjects obtained from the GEO were produced by analysis using GeneChip® U133A (Affymetrix, Inc.), a DNA chip. The DNA chip has 22,283 probe sets, which include probe sets for the same gene.

Concerning the same gene for which a plurality of probe sets are provided on the DNA chip, therefore, only a probe set showing the maximum signal value was taken from the probe sets for the same gene. In addition, probe sets with a signal value of 50 or less were also excluded, because the reproducibility of the measured values was considered to be low. As a result, genes for 9,331 probe sets were subjected to the analysis described below.

Example 1 (Method for Determining the Presence of Crohn's Disease)

(1) Identification of Crohn's Disease-Determining Gene Families

Data available from the Gene Expression Omnibus (GEO, ncbi.nlm.nih.gov/geo), which was a gene expression data bank, were used in Example 1, which were data on the levels of expression of gene transcription products in the blood of Crohn's disease patients and healthy subjects. The data were normalized data obtained by normalization of raw measured signal data, which are available from ncbi.nlm.nih.gov/sites/GDSbrowser?acc=GDS1615.

(1-1) Selection of Samples and Probe Sets

Data on Crohn's disease patients 1 (29 samples) and data on healthy subjects 1 (21 samples) were randomly selected from the data described above, and these data were used to identify Crohn's disease-determining gene families.

The data on Crohn's disease patients and healthy subjects obtained from the GEO were produced by analysis using GeneChip® U133A (Affymetrix, Inc.), a DNA chip. The DNA chip has 22,283 probe sets, which include probe sets for the same gene.

Concerning the same gene for which a plurality of probe sets are provided on the DNA chip, therefore, only a probe set showing the maximum signal value was taken from the probe sets for the same gene. In addition, probe sets with a signal value of 50 or less were also excluded, because the reproducibility of the measured values was considered to be low. As a results, genes for 9,331 probe sets were subjected to the analysis described below.

(1-3) Gene Classification and Obtaining Average for Each Gene Family

The 9,331 genes were classified into gene families (GO Terms) based on the classification of Gene Ontology (available from geneontology.org/index.shtml), and the average of the z-scores for the Crohn's disease patients 1 (29 samples) obtained in the section (1-2) was calculated with respect to the gene within each GO Term.

(1-4) Selecting Gene Families Having Significant Difference Between Healthy Subjects and Crohn's Disease Patients A t-test was performed using the averages obtained as described above for the healthy subjects and the Crohn's disease patients with respect to each GO Term, so that a significance probability (p-value) was obtained.

GO Terms for which the resulting p-value was 0.05 or less (p-value≤5.0E-02) were extracted from the GO Terms used.

Subsequently, hierarchical clustering was performed using the z-scores for all genes contained in the extracted GO Terms, and synchronously varying gene clusters were selected. The clustering was performed using software Cluster 3.0 (available from bonsai.ims.u-tokyo.ac.jp/~mdehoon/software/cluster/software.htm), and the result was displayed using Java Tree View (available from sourceforge.net/projects/jtreeview/files/).

The average of the z-scores for the gene contained in each cluster was used as a cluster score, when a t-test was performed on the healthy subjects 1 (21 samples) and the Crohn's disease patients 1 (29 samples). From the clusters for which the resulting p-value was 0.05 or less, the G protein-related gene family, blood coagulation-related gene family, oxidative stress-related gene family, phagocytosis-related gene family, and fat oxidation-related gene family were selected as Crohn's disease-determining gene families. Table 2 shows these gene families, genes belonging to each family, and the p-value for each family.

Figure 5:
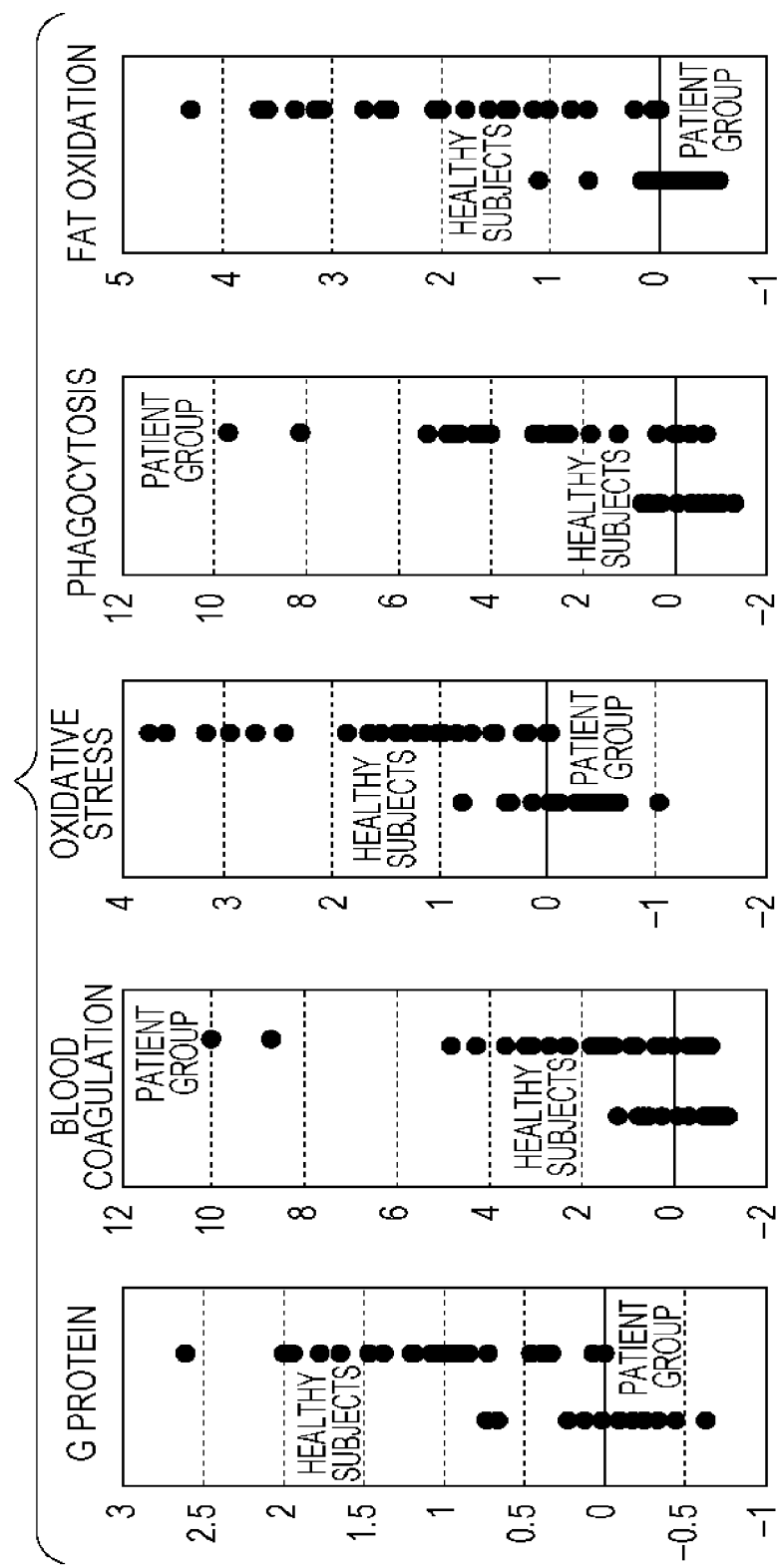
FIG. 5 shows the distribution of the average of z-scores for healthy subjects and Crohn's disease patients calculated from the levels of expression of transcription products of genes belonging to a G protein-related gene family, a blood coagulation-related gene family, an oxidative stress-related gene family, a phagocytosis-related gene family, and a fat oxidation-related gene family.

FIG. 5 shows the distribution of the average of the z-scores for the healthy subjects 1 and the Crohn's disease patients 1 with respect to each gene family selected as described above.

TABLE 2

| Gene families | Gene symbol | Gene title |
|---|---|---|
| G protein (p = 1.20E-12) | GNG3 | guanine nucleotide binding protein (G protein), gamma 3 |
| | GNG7 | guanine nucleotide binding protein (G protein), gamma 7 |
| | GNA15 | guanine nucleotide binding protein (G protein), alpha 15 (Gq class) |
| | GNB5 | guanine nucleotide binding protein (G protein), beta 5 |
| | GNAS | GNAS complex locus |
| | GNG5 | guanine nucleotide binding protein (G protein), gamma 5 |
| | GNG11 | guanine nucleotide binding protein (G protein), gamma 11 |
| | GNB1 | guanine nucleotide binding protein (G protein), beta polypeptide 1 |
| | GNG4 | guanine nucleotide binding protein (G protein), gamma 4 |
| Blood coagulation (p = 4.70E-05) | GP1BA | glycoprotein Ib (platelet), alpha polypeptide |
| | GP1BB | glycoprotein Ib (platelet), beta polypeptide /// septin 5 |
| | ITGB3 | integrin, beta 3 (platelet glycoprotein IIIa, antigen CD61) |
| | GP9 | glycoprotein IX (platelet) |
| | F13A1 | coagulation factor XIII, A1 polypeptide |

TABLE 2-continued

| Gene families | Gene symbol | Gene title |
|---|---|---|
| Fat oxidation (p = 3.80E−10) | ACOX1 | acyhCoenzyme A oxidase 1, palmitoyl |
| | ADIPOR2 | adiponectin receptor 2 |
| | ADIPOR1 | adiponectin receptor 1 |
| | ALOX12 | arachidonate 12-lipoxygenase |
| Oxidative stress) (p = 6.90E−10 | GPX1 | glutathione peroxidase 1 |
| | PTGS1 | prostaglandin-endoperoxide synthase 1 (prostaglandin G/H synthase and cyclooxygenase) |
| | CLU | clusterin |
| | PDLIM1 | PDZ and LIM domain 1 |
| Phagocytosis (p = 2.00E−07) | FCER1G | Fc fragment of IgE, high affinity I, receptor for; gamma polypeptide |
| | CLEC7A | C-type lectin domain family 7, member A |
| | VAMP7 | vesicle-associated membrane protein 7 |
| | FCGR1A | Fc fragment of IgG, high affinity Ia, receptor (CD64) /// Fc fragment of IgG, high affinity Ic, receptor (CD64) |

(2) Evaluating the Accuracy of the Determination Method of the Invention (2-1) Determination for the Samples Used in the Identification of Crohn's Disease-Determining Gene Families The averages for the healthy subjects 1 (21 samples) and the Crohn's disease patients 1 (29 samples) with respect to each of the five Crohn's disease-determining gene families were each input to a support vector machine (SVM incorporated in statistical analysis software GeneSpring). The SVM containing the input averages for the 50 samples was then used to determine whether each sample was positive (or had Crohn's disease) or negative (or healthy).

The result is shown in FIG. 6A. In FIG. 6A, "sensitivity" is the rate at which the Crohn's disease patients are determined to be "positive," and "specificity" is the rate at which the healthy subjects are correctly identified. In the drawing, "concordance rate" is the rate at which the Crohn's disease patients and the healthy subjects are determined to be "positive (+)" and "negative (−)," respectively. The result shows that the determination method of the invention makes it possible to identify Crohn's disease patients and healthy subjects at a sensitivity of 90% or more and a specificity of 90% or more.

(2-2) Evaluating the Reproducibility of the Determination Method of the Invention Additionally, data on Crohn's disease patients 2 (30 samples) and healthy subjects 2 (21 samples), which were different from the data selected in the section (1-1), were used to evaluate the reproducibility of the determination method of the invention. The determination was performed on these data using the SVM containing the input averages for the samples used in the identification of Crohn's disease-determining gene families in the section (2-1).

The result is shown in FIG. 6B. The result shows that even for samples different from those used in the identification of Crohn's disease-determining gene families, the determination method of the invention makes it possible to stably distinguish between healthy subjects and Crohn's disease patients at a sensitivity of 95% or more and a specificity of 90% or more.

Comparative Example 1(Determination of the Presence of Crohn's Disease by Conventional Determination Method)

In this comparative example, a method of determining the presence of a disease directly based on the levels of expression of gene transcription products in healthy subjects and patients was used as a conventional determination method. The accuracy of the determination of the presence of Crohn's disease by such a conventional method was evaluated.

(1) Determination Using Genes Belonging to Crohn's Disease-determining Gene Families (1-1) Samples Used in the Identification of Crohn's Disease-Determining Gene Families The expression levels in the healthy subjects 1 (21 samples) and the Crohn's disease patients 1 (29 samples) with respect to each of the 26 genes in Table 1 were input to the SVM. The accuracy of determining whether each sample was positive or negative was evaluated using the SVM containing the input expression levels in the 50 samples.

The result is shown in FIG. 7A. The result shows that the conventional method identified the Crohn's disease patients and the healthy subjects at a sensitivity of 100% and a specificity of 100%.

(1-2) Evaluating the Reproducibility of the Conventional Determination Method

Data on Crohn's disease patients 2 (30 samples) and healthy subjects 2 (21 samples) were then used to evaluate the reproducibility of the conventional determination method. The determination was performed on these samples using the SVM to which the expression levels in the healthy subjects 1 (21 samples) and the Crohn's disease patients 1 (29 samples) were input in the section (1-1).

The result is shown in FIG. 7B. The result shows that for samples different from those used in the identification of Crohn's disease-determining gene families, the specificity of the conventional determination method was reduced to 65% or less, although the sensitivity was 90% or more. It is therefore apparent that the conventional determination method is more likely to misidentify healthy subjects as Crohn's disease patients than the determination method of the invention.

(2) Determination Using Genes Other than those Belonging to Crohn's Disease-Determining Gene Families (2-1) Samples Used in the Identification of Crohn's Disease-Determining Gene Families Genes other than those belonging to Crohn's disease-determining gene families (26 genes in Table 1) were further identified so that an examination could be performed using such genes. Specifically, a t-test was performed to calculate the significance probability (p-value) between the expression levels in the healthy subjects 1 (21 samples) and the Crohn's disease patients 1 (29 samples), and the gene for which the resulting p-value was 0.05 or less with respect to the expression level was determined to be used for the determination. As a result, five genes were identified. Table 3 shows these genes and the p-value for each gene. FIG. 8 also shows the distribution of the level of expression of the transcription product of each gene in the healthy subjects 1 and the Crohn's disease patients 1.

TABLE 3

| Probe set ID | Gene symbol | Gene title | |
|---|---|---|---|
| 202162_s_at | CNOT8 | CCR4-NOT transcription complex, subunit 8 | 8.06E−15 |
| 200828_s_at | ZNF207 | zinc finger protein 207 | 8.60E−15 |
| 201133_s_at | PJA2 | praja ring finger 2 | 5.92E−14 |
| 204725_s_at | NCK1 | NCK adaptor protein 1 | 1.11E−13 |
| 203432_at | AW272611 | thymopoietin | 3.16E−13 |

The expression levels in the healthy subjects 1 (21 samples) and the Crohn's disease patients 1 (29 samples)

with respect to each of these genes were each input to the SVM. The accuracy of determining whether each sample was positive or negative was evaluated using the SVM containing the input expression levels in the 50 samples.

The result is shown in FIG. 9A. The result shows that the conventional method using genes other than those belonging to Crohn's disease-determining gene families identified the Crohn's disease patients and the healthy subjects at a sensitivity of 95% or more and a specificity of 95% or more.

(2-2) Evaluating the Reproducibility of the Conventional Determination Method

Data on the Crohn's disease patients 2 (30 samples) and the healthy subjects 2 (21 samples) were then used to evaluate the reproducibility of the conventional determination method using the five genes. The determination was performed on these samples using the SVM to which the expression levels in the healthy subjects 1 (21 samples) and the Crohn's disease patients 1 (29 samples) were input in the section (2-1).

The result is shown in FIG. 9B. The result shows that for samples different from those used in the identification of Crohn's disease-determining gene families, the specificity of the conventional determination method was reduced to 40% or less, although the sensitivity was 90% or more. It is therefore apparent that the conventional determination method using genes other than those belonging to Crohn's disease-determining gene families is more likely to misidentify healthy subjects as Crohn's disease patients than the determination method of the invention.

The results of Example 1 and Comparative Example 1 show that the determination method of the invention can achieve more accurate and more stable determination than conventional methods in which the presence of Crohn's disease is determined directly based on the levels of expression of gene transcription products in healthy subjects and Crohn's disease patients.

Example 2 (Method for Determining the Presence of Huntington's Disease)

(1) Identification of Huntington's Disease-Determining Gene Families

Data obtained from GEO were used in Example2, which were data on the levels of expression of gene transcription products in the blood of Huntington's disease patients and healthy subjects. The data were normalized data obtained by normalization of raw measured signal data, which are available from ncbi.nlm.nih.gov/geo/query/acc.cgi?acc=GSE1751.

(1-1) Selection of Samples and Probe Sets

Data on Huntington's disease patients 1 (6 samples) and data on healthy subjects 3 (7 samples) were randomly selected from the data described above, and these data were used to identify Huntington's disease-determining gene families.

The data on Huntington's disease patients and healthy subjects obtained from the GEO were produced by analysis using GeneChip® U133A (Affymetrix, Inc.). Similarly to the section (1-1) of Example 1, concerning the same gene for which a plurality of probe sets are provided on the DNA chip, only a probe set showing the maximum signal value was taken from the probe sets for the same gene. In addition, probe sets with a signal value of 50 or less were also excluded, because the reproducibility of the measured values was considered to be low. As a result, genes for 8,370 probe sets were subjected to the analysis described below.

(1-2) Obtaining Expression Level z-Scores

Averages and standard deviations were calculated using all signal values obtained from the healthy subjects 3 (7 samples) with respect to transcription products of the genes for the 8,370 probe sets selected as described above. Values representing deviations (z-scores) were calculated for each of the 8,370 genes using these values and the following formula: z-score={(the signal value of the transcription product of each gene)−(the average of the signal values of the transcription product of the corresponding gene in the healthy subjects 3 (7 samples))}/(the standard deviation of the signal values of the transcription product of the corresponding gene in the healthy subjects 3 (7 samples))

(1-3) Gene Classification and Obtaining Average for Each Gene Family

The 8,370 genes were classified into gene families (GO Terms) based on the classification of Gene Ontology, and the average of the z-scores for the Huntington's disease patients 1 (6 samples) obtained in the section (1-2) was calculated with respect to the gene within each GO Term.

The average of the z-scores for the healthy subjects 3 (7 samples) was also calculated in the same manner with respect to the gene within each GO Term.

(1-4) Selecting Gene Families Having Significant Difference Between Healthy Subjects and Huntington's Disease Patients A t-test was performed using the averages obtained as described above for the healthy subjects and the Huntington's disease patients with respect to each GO Term, so that a significance probability (p-value) was obtained.

GO Terms for which the resulting p-value was 0.05 or less (p-value≤5.0E-02) were extracted from the GO Terms used.

Subsequently, hierarchical clustering was performed using the z-scores for all genes contained in the extracted GO Terms, and synchronously varying gene clusters were selected. The clustering was performed using software Cluster 3.0 (available from bonsai.ims.u-tokyo.ac.jp/~mdehoon/software/cluster/software.htm), and the result was displayed using Java Tree View (available from sourceforge.net/projects/jtreeview/files/).

The average of the z-scores for the gene contained in each cluster was used as a cluster score, when a t-test was performed on the healthy subjects 3 (7 samples) and the Huntington's disease patients 1 (6 samples). From the clusters for which the resulting p-value was 0.05 or less, the microtubule-related gene family, mitochondria-related gene family, and prostaglandin-related gene family were selected as Huntington's disease-determining gene families. Table 4 shows these gene families, genes belonging to each family, and the p value for each family.

Figure 10:
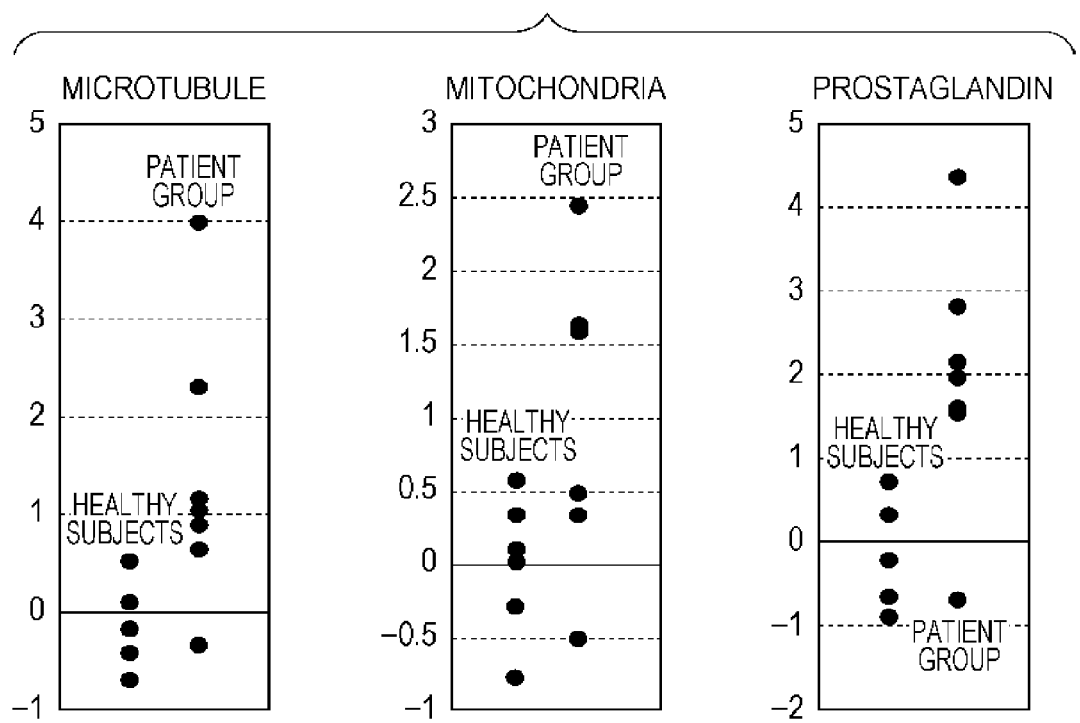
FIG. 10 shows the distribution of the average of z-scores for healthy subjects and Huntington's disease patients calculated from the levels of expression of transcription products of genes belonging to a microtubule-related gene family, a mitochondria-related gene family, and a prostaglandin-related gene family.

FIG. 10 shows the distribution of the average of the z-scores for the healthy subjects 3 and the Huntington's disease patients 1 with respect to each gene family selected as described above.

TABLE 4

| Gene families | Gene symbol | Gene title |
| --- | --- | --- |
| Microtubule (p = 2.62E−02) | DYNC1LI1 | dynein, cytoplasmic 1, light intermediate chain 1 |
| | DYNLL1 | dynein, light chain, LC8-type 1 |
| | DYNLT1 | dynein, light chain, Tctex-type 1 |
| | DYNLT3 | dynein, light chain, Tctex-type 3 |
| Mitochondria (p = 3.28E−02) | ATP5F1 | ATP synthase, H+ transporting, mitochondrial F0 complex, subunit B1 |
| | ATP5J | ATP synthase, H+ transporting, mitochondrial F0 complex, subunit F6 |
| | ATP5L | ATP synthase, H+ transporting, mitochondrial F0 complex, subunit G |

TABLE 4-continued

| Gene families | Gene symbol | Gene title |
|---|---|---|
| | ATP5C1 | ATP synthase, H+ transporting, mitochondrial F1 complex, gamma polypeptide 1 |
| | ATP5O | ATP synthase, H+ transporting, mitochondrial F1 complex, O subunit (oligomycin sensitivity conferring protein) |
| | COX6A1 | cytochrome c oxidase subunit VIa polypeptide 1 |
| | COX7A2 | cytochrome c oxidase subunit VIIa polypeptide 2 (liver) |
| | CYCS | cytochrome c, somatic |
| | MRPL18 | mitochondrial ribosomal protein L18 |
| | MRPS35 | mitochondrial ribosomal protein S35 |
| | NDUFA4 | NADH dehydrogenase (ubiquinone) 1 alpha subcomplex, 4, 9 kDa |
| | NDUFA9 | NADH dehydrogenase (ubiquinone) 1 alpha subcomplex, 9, 39 kDa |
| | NDUFB1 | NADH dehydrogenase (ubiquinone) 1 beta subcomplex, 1, 7 kDa |
| | NDUFB3 | NADH dehydrogenase (ubiquinone) 1 beta subcomplex, 3, 12 kDa |
| | NDUFB5 | NADH dehydrogenase (ubiquinone) 1 beta subcomplex, 5, 16 kDa |
| | NDUFC1 | NADH dehydrogenase (ubiquinone) 1, subcomplex unknown, 1, 6 kDa |
| | NDUFS4 | NADH dehydrogenase (ubiquinone) Fe—S protein 4, 18 kDa (NADH-coenzyme Q reductase) |
| | TIMM17A | translocase of inner mitochondrial membrane 17 homolog A |
| | TIMM8B | translocase of inner mitochondrial membrane 8 homolog B |
| | TOMM20 | translocase of outer mitochondrial membrane 20 homolog |
| | TOMM7 | translocase of outer mitochondrial membrane 7 homolog |
| | UQCRH | ubiquinol-cytochrome c reductase hinge protein |
| | UQCR | ubiquinol-cytochrome c reductase, 6.4 kDa subunit |
| | UQCRQ | ubiquinol-cytochrome c reductase, complex III subunit VII, 9.5 kDa |
| Prostaglandin (p = 7.84E−03) | PTGER2 | prostaglandin E receptor 2 (subtype EP2), 53 kDa |
| | PTGER4 | prostaglandin E receptor 4 (subtype EP4) |
| | PTGES3 | prostaglandin E synthase 3 (cytosolic) |

(2) Evaluating the Accuracy of the Determination Method of the Invention (2-1) Determination for the Samples Used in the Identification of Huntington's Disease-Determining Gene Families The averages for the healthy subjects 3 (7 samples) and the Huntington's disease patients 1 (6 samples) with respect to each of the three Huntington's disease-determining gene families were each input to a SVM. The SVM containing the input averages for the 13 samples was then used to determine whether each sample was positive (or had Huntington's disease) or negative (or healthy).

The result is shown in FIG. 11A. The result shows that the determination method of the invention makes it possible to identify Huntington's disease patients and healthy subjects at a sensitivity of 100% and a specificity of 100%.

(2-2) Evaluating the Reproducibility of the Determination Method of the Invention Additionally, data on Huntington's disease patients 2 (6 samples) and healthy subjects 4 (7 samples), which were different from the data selected in the section (1-1), were used to evaluate the reproducibility of the determination method of the invention. The determination was performed on these data using the SVM containing the input averages for the samples used in the identification of Huntington's disease-determining gene families in the section (2-1).

The result is shown in FIG. 11B. The result shows that even for samples different from those used in the identification of Huntington's disease-determining gene families, the determination method of the invention makes it possible to stably distinguish between healthy subjects and Huntington's disease patients at a sensitivity of 80% or more and a specificity of 100%.

Comparative Example 2(Determination of the Presence of Huntington's Disease by Conventional Determination Method)

In this comparative example, a method of determining the presence of a disease directly based on the levels of expression of gene transcription products in healthy subjects and patients was used as a conventional determination method. The accuracy of the determination of the presence of Huntington's disease by such a conventional method was evaluated.

(1) Determination Using Genes Belonging to Huntington's Disease-Determining Gene Families (1-1) Samples Used in the Identification of Huntington's Disease-Determining Gene Families The expression levels in the healthy subjects 3 (7 samples) and the Huntington's disease patients 1 (6 samples) with respect to each of the 27 genes in Table 3 were input to the SVM. The accuracy of determining whether each sample was positive or negative was evaluated using the SVM containing the input expression levels in the 13 samples.

The result is shown in FIG. 12A. The result shows that the conventional method identified the Huntington's disease patients and the healthy subjects at a sensitivity of 100% and a specificity of 100%.

(1-2) Evaluating the Reproducibility of the Conventional Determination Method

Data on the Huntington's disease patients 2 (6 samples) and healthy subjects 4 (7 samples) were then used to evaluate the reproducibility of the conventional determination method. The determination was performed on these samples using the SVM to which the expression levels in the healthy subjects 3 (7 samples) and the Huntington's disease patients 1 (6 samples) were input in the section (1-1).

The result is shown in FIG. 12B. The result shows that for samples different from those used in the identification of Huntington's disease-determining gene families, the sensitivity of the conventional determination method was reduced to 70% or less, although the specificity was 100%. It is therefore apparent that the conventional determination method is more likely to misidentify Huntington's disease patients as healthy subjects than the determination method of the invention.

(2) Determination Using Genes Other than Those Belonging to Huntington's Disease-Determining Gene Families (2-1) Samples Used in the Identification of Huntington's Disease-Determining Gene Families Genes other than those belonging to Huntington's disease-determining gene families (27 genes in Table 3) were further identified so that an examination could be performed using such genes. Specifically, a t-test was performed to calculate the significance probability (p-value) between the expression levels in the healthy subjects 3 (7 samples) and the Huntington's disease patients 1 (6 samples), and the gene for which the resulting p-value was 0.05 or less with respect to the expression level was determined to be used for the determination. As a result, ten genes were identified. Table 5 shows these genes and the p-value for each gene. FIG. 13 also shows the distribution of the level of expression of the transcription product of each gene in the healthy subjects 3 and the Huntington's disease patients 1.

TABLE 5

| ProbeSet ID | Gene symbol | Gene title | p-value |
|---|---|---|---|
| 203909_at | SLC9A6 | solute carrier family 9 (sodium/hydrogen exchanger), member 6 | 6.59E−07 |
| 219065_s_at | MEMO1 | mediator of cell motility 1 | 2.26E−06 |
| 218854_at | DSE | dermatan sulfate epimerase | 2.63E−06 |
| 220933_s_at | ZCCHC6 | zinc finger, CCHC domain containing 6 | 3.26E−06 |
| 203024_s_at | C5orf15 | chromosome 5 open reading frame 15 | 4.00E−06 |
| 208801_at | SRP72 | signal recognition particle 72 kDa | 5.40E−06 |
| 215492_x_at | LOC441150 | similar to RIKEN cDNA 2310039H08///ribosomal protein L7-like 1 ///pre T-cell antigen receptor alpha ///KIAA0240 ///canopy 3 homolog | 8.86E−06 |
| 208335_s_at | DARC | Duffy blood group, chemokine receptor | 1.12E−05 |
| 203474_at | IQGAP2 | IQ motif containing GTPase activating protein 2 | 1.29E−05 |
| 218005_at | ZNF22 | zinc finger protein 22 (KOX 15) | 1.31E−05 |

The expression levels in the healthy subjects 3 (7 samples) and the Huntington's disease patients 1 (6 samples) with respect to each of these genes were input to the SVM. The accuracy of determining whether each sample was positive or negative was evaluated using the SVM containing the input expression levels in the 13 samples.

The result is shown in FIG. 14A. The result shows that the conventional method using genes other than those belonging to Huntington's disease-determining gene families identified the Huntington's disease patients and the healthy subjects at a sensitivity of 100% and a specificity of 100%.

(2-2) Evaluating the Reproducibility of the Conventional Determination Method

Data on the Huntington's disease patients 2 (6 samples) and the healthy subjects 4 (7 samples) were then used to evaluate the reproducibility of the conventional determination method using the ten genes. The determination was performed on these samples using the SVM to which the expression levels in the healthy subjects 3 (7 samples) and the Huntington's disease patients 1 (6 samples) were input in the section (2-1).

The result is shown in FIG. 14B. The result shows that for samples different from those used in the identification of Huntington's disease-determining gene families, the sensitivity of the conventional determination method was reduced to 50%, although the specificity was 100%. It is therefore apparent that the conventional determination method using genes other than those belonging to Huntington's disease-determining gene families is more likely to misidentify Huntington's disease patients as healthy subjects than the determination method of the invention.

The results of Example 2 and Comparative Example 2 show that the determination method of the invention can achieve more accurate and more stable determination than conventional methods in which the presence of Huntington's disease is determined directly based on the levels of expression of gene transcription products in healthy subjects and Huntington's disease patients.

Example 3 (Method for Determining the Presence of Endometriosis) (1) Identification of Endometriosis-Determining Gene Families Data obtained from GEO were used in Example 3, which were data on the levels of expression of gene transcription products in normal tissues and lesion tissues of endometriosis patients. The data were normalized data obtained by normalization of raw measured signal data, which are available from ncbi.nlm.nih.gov/geo/query/acc.cgi?acc=GSE7305 and ncbi.nlm.nih.gov/geo/query/acc.cgi?acc=GSE6364.

(1-1) Selection of Samples and Probe Sets

Data on lesion tissues 1 (9 samples) and data on normal tissues 1 (8 samples) were randomly selected from the data described above, and these data were used to identify endometriosis-determining gene families.

The data on lesion tissues and normal tissues obtained from the GEO were produced by analysis using GeneChip® U133 plus2.0 (Affymetrix, Inc.), a DNA chip. The DNA chip has 54,675 probe sets, which include probe sets for the same gene.

Concerning the same gene for which a plurality of probe sets are provided on the DNA chip, therefore, only a probe set showing the maximum signal value was taken from the probe sets for the same gene. In addition, probe sets with a signal value of 100 or less were also excluded, because the reproducibility of the measured values was considered to be low. As a result, genes for 16,207 probe sets were subjected to the analysis described below.

(1-2) Obtaining Expression Level z-Scores

Averages and standard deviations were calculated using all signal values obtained from the normal tissues 1 (8 samples) with respect to transcription products of the genes for the 16,207 probe sets selected as described above. Values representing deviations (z-scores) were calculated for each of the 16,207 genes using these values and the following formula: z-score={(the signal value of the transcription product of each gene)−(the average of the signal values of the transcription product of the corresponding gene in the normal tissues 1 (8 samples))}/(the standard deviation of the signal values of the transcription product of the corresponding gene in the normal tissues 1 (8 samples))

(1-3) Gene Classification and Obtaining Average for Each Gene Family

The 16,207 genes were classified into gene families (GO Terms) based on the classification of Gene Ontology, and the average of the z-scores for the lesion tissues 1 (9 samples) obtained in the section (1-2) was calculated with respect to the gene within each GO Term.

The average of the z-scores for the normal tissues 1 (8 samples) was also calculated in the same manner with respect to the gene within each GO Term.

(1-4) Selecting Gene Families Having Significant Difference Between Normal Tissues and Lesion Tissues A t-test was performed using the averages obtained as described above for the normal tissues and the lesion tissues with respect to each GO Term, so that a significance probability (p-value) was obtained.

GO Terms for which the resulting p-value was 0.05 or less (p-value≤5.0E-02) were extracted from the GO Terms used.

Subsequently, hierarchical clustering was performed using the z-scores for all genes contained in the extracted GO Terms, and synchronously varying gene clusters were selected. The clustering was performed using software Cluster 3.0 (available from bonsai.ims.u-tokyo.ac.jp/~mdehoon/software/cluster/software.htm), and the result was displayed using Java Tree View (available from sourceforge.net/projects/jtreeview/files/).

The average of the z-scores for the gene contained in each cluster was used as a cluster score, when a t-test was performed on the normal tissues 1 (8 samples) and the lesion tissues 1 (9 samples). From the clusters for which the resulting p-value was 0.05 or less, the cytokine synthesis process-related gene family, cytokine-mediated signaling-related gene family, and immunoglobulin-mediated immune response-related gene family were selected as endometriosis-determining gene families. Table 6 shows these gene families, genes belonging to each family, and the p-value for each family.

Figure 15:
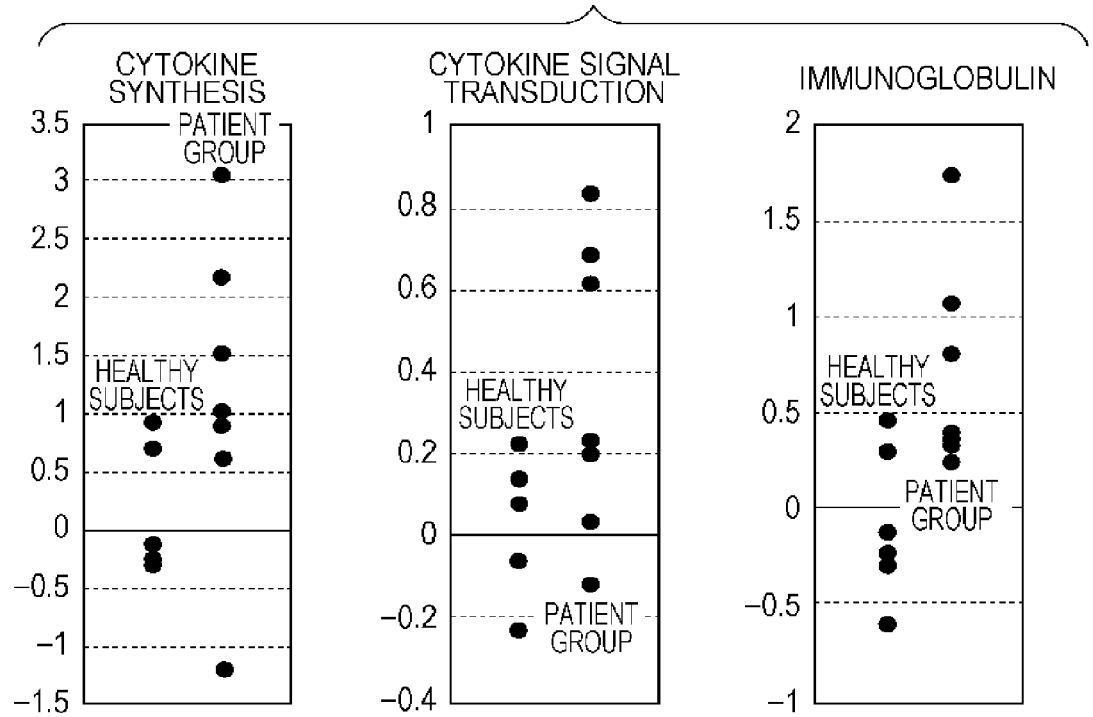
FIG. 15 shows the distribution of the average of z-scores for normal tissues and endometriosis lesion tissues calculated from the levels of expression of transcription products of genes belonging to a cytokine synthesis process-related gene family, a cytokine-mediated signaling-related gene family, and an immunoglobulin-mediated immune response-related gene family.

FIG. 15 shows the distribution of the average of the z-scores for the normal tissues 1 and the lesion tissues 1 with respect to each gene family selected as described above.

samples was then used to determine whether each sample was positive (or had endometriosis) or negative (or healthy).

The result is shown in FIG. 16A. The result shows that the determination method of the invention makes it possible to identify samples with lesion tissues and samples with normal tissues at a sensitivity of 85% or more and a specificity of 100%.

(2-2) Evaluating the Reproducibility of the Determination Method of the Invention Additionally, data on lesion tissues 2 (9 samples) and normal tissues 2 (8 samples), which were different from the data selected in the section (1-1), were used to evaluate the reproducibility of the determination method of the invention. The determination was performed on these data using the SVM containing the input averages for the samples used in the identification of endometriosis-determining gene families in the section (2-1).

TABLE 6

| Gene families | Gene symbol | Gene title |
|---|---|---|
| Gytokine synthesis process ($p = 1.25E-03$) | CEBPE | CCAAT/enhancer binding protein (C/EBP), epsilon |
| | CD28 | CD28 molecule |
| Cytokine-mediated signaling pathway ($p = 4.10E-03$) | EREG | epiregulin |
| | STAT3 | signal transducer and activator of transcription 3 (acute-phase response factor) |
| | STAT5A | signal transducer and activator of transcription 5A |
| | STAT5B | signal transducer and activator of transcription 5B |
| | SOCS1 | suppressor of cytokine signaling 1 |
| | SOCS5 | suppressor of cytokine signaling 5 |
| | RELA | v-rel reticuloendotheliosis viral oncogene homolog A, p65 (avian), nuclear factor of kappa light polypeptide gene enhancer in B-cells 3, |
| | CEBPA | CCAAT/enhancer binding protein (C/EBP), alpha |
| | DUOX2 | dual oxidase 2 |
| | DUOX1 | dual oxidase 1 |
| | STAT4 | signal transducer and activator of transcription 4 |
| | ZNF675 | zinc finger protein 675 |
| | IL2RB | interleukin 2 receptor, beta |
| | IRAK3 | interleukin-1 receptor-associated kinase 3 |
| | KIT | v-kit Hardy-Zuckerman 4 feline sarcoma viral oncogene homolog |
| | LRP8 | low density lipoprotein receptor-related protein 8, apolipoprotein e receptor |
| | TNFRSF1A | tumor necrosis factor receptor superfamily, member 1A |
| | PLP2 | proteolipid protein 2 (colonic epithelium-enriched) |
| | TNFRSF1B | tumor necrosis factor receptor superfamily, member 1B |
| | TGM2 | transglutaminase 2 (C polypeptide, protein-glutamine-gamma-glutamyltransferase) |
| | CCR1 | chemokine (C-C motif) receptor 1 |
| | CCR2 | chemokine (C-C motif) receptor 2 |
| | PF4 | platelet factor 4 (chemokine (C-X-C motif) ligand 4) |
| | CX3CL1 | chemokine (C-X3-C motif) ligand 1 |
| | IL1R1 | interleukin 1 receptor, type I |
| | CSF2RB | colony stimulating factor 2 receptor, beta, low-affinity (granulocyte-macrophage) |
| | CLCF1 | cardiotrophinlike cytokine factor 1 |
| | NUP85 | nucleoporin 85 kDa |
| Immunoglobulin-mediated immune response ($p = 7.50E-03$) | IGHG3 | immunoglobulin heavy constant gamma 3 (G3m marker) |
| | IGHM | immunoglobulin heavy constant mu |
| | CD74 | CD74 molecule, major histocompatibility complex, class II invariant chain |
| | FCER1G | Fc fragment of IgE, high affinity I, receptor for; gamma polypeptide |
| | BCL10 | B-cell CLL/lymphoma 10 |
| | PRKCD | protein kinase C, delta |
| | CD27 | CD27 molecule |
| | MYD88 | myeloid differentiation primary response gene (88) |
| | TLR8 | toll-like receptor 8 |

(2) Evaluating the Accuracy of the Determination Method of the Invention (2-1) Determination for the Samples Used in the Identification of Endometriosis-Determining Gene Families The averages for the normal tissues 1 (8 samples) and the lesion tissues 1 (9 samples) with respect to each of the three endometriosis-determining gene families were each input to a SVM. The SVM containing the input averages for the 17

The result is shown in FIG. 16B. The result shows that even for samples different from those used in the identification of endometriosis-determining gene families, the determination method of the invention makes it possible to stably distinguish between samples with normal tissues and samples with lesion tissues at a sensitivity of 75% and a specificity of 85% or more.

Comparative Example 3(Determination of the Presence of Endometriosis by Conventional Determination Method)

In this comparative example, a method of determining the presence of a disease directly based on the levels of expression of gene transcription products in healthy subjects and patients was used as a conventional determination method. The accuracy of the determination of the presence of endometriosis lesion tissues in samples by such a conventional method was evaluated.

(1) Determination Using Genes Belonging to Endometriosis-Determining Gene Families (1-1) Samples Used in the Identification of Endometriosis-Determining Gene Families The expression levels in the normal tissues 1 (8 samples) and the lesion tissues 1 (9 samples) with respect to each of the 39 genes in Table 5 were input to the SVM. The accuracy of determining whether each sample was positive or negative was evaluated using the SVM containing the input expression levels in the 17 samples.

The result is shown in FIG. 17A. The result shows that the conventional method identified the normal tissues and the lesion tissues at a sensitivity of 100% and a specificity of 100%.

(1-2) Evaluating the Reproducibility of the Conventional Determination Method

Data on the normal tissues 2 (8 samples) and lesion tissues 2 (9 samples) were then used to evaluate the reproducibility of the conventional determination method. The determination was performed on these samples using the SVM to which the expression levels in the normal tissues 1 (8 samples) and the lesion tissues 1 (9 samples) were input in the section (1-1).

The result is shown in FIG. 17B. The result shows that for samples different from those used in the identification of endometriosis-determining gene families, the sensitivity of the conventional determination method was reduced to 65% or less, although the specificity was 100%. It is therefore apparent that the conventional determination method is more likely to misidentify endometriosis patients as healthy subjects than the determination method of the invention.

Figure 18:
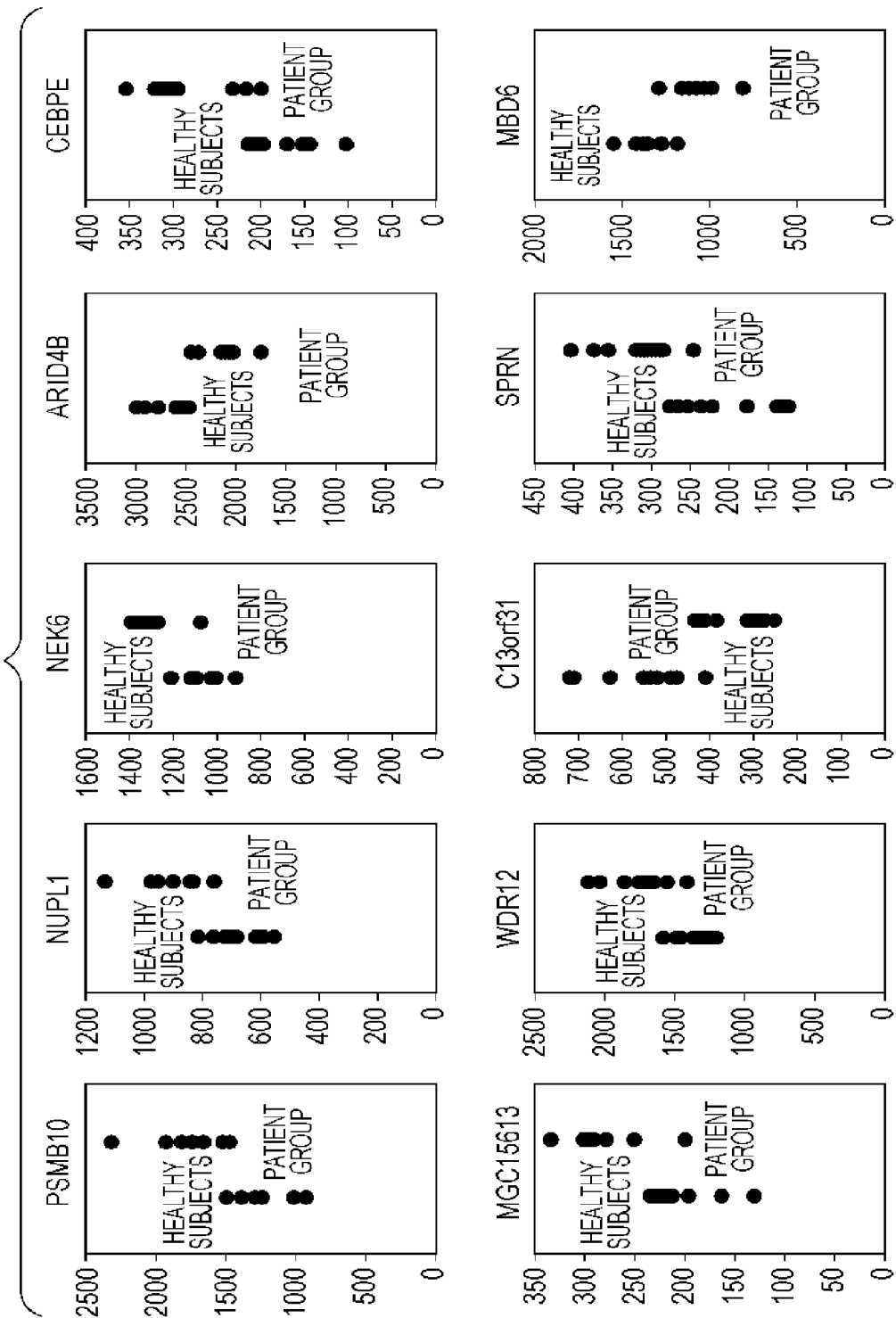
FIG. 18 shows the distributions of the levels of expression of genes which are identified as having a significant difference between normal tissues and endometriosis lesion tissues from data on the levels of expression of gene transcription products in normal tissues and endometriosis lesion tissues, which are the same as those used in the identification of endometriosis-determining gene families.

(2) Determination Using Genes Other than Those Belonging to Endometriosis-Determining Gene Families (2-1) Samples Used in the Identification of Endometriosis-Determining Gene Families Genes other than those belonging to endometriosis-determining gene families (39 genes in Table 5) were further identified so that an examination could be performed using such genes. Specifically, a t-test was performed to calculate the significance probability (p-value) between the expression levels in the normal tissues 1 (8 samples) and the lesion tissues 1 (9 samples), and the gene for which the resulting p-value was 0.05 or less with respect to the expression level was determined to be used for the determination. As a result, ten genes were identified. Table 7 shows these genes and the p-value for each gene. FIG. 18 also shows the distribution of the level of expression of the transcription product of each gene in the normal tissues 1 and the lesion tissues 1.

TABLE 7

| ProbeSet ID | Gene symbol | Gene title | P value |
| --- | --- | --- | --- |
| 202659_at | PSMB10 | proteasome (prosome, macropain) subunit, beta type, 10 | 1.08E−04 |
| 241425_at | NUPL1 | nucleoporin like 1 | 1.50E−04 |
| 223158_s_at | NEK6 | myeloproliferative disease associated tumor antigen 5 ///NIMA (never in mitosis gene a)-related kinase 6 | 1.62E−04 |

TABLE 7-continued

| ProbeSet ID | Gene symbol | Gene title | P value |
| --- | --- | --- | --- |
| 221230_s_at | ARID4B | AT rich interactive domain 4B (RBP1-like) | 1.76E−04 |
| 214523_at | CEBPE | CCAAT/enhancer binding protein (C/EBP), epsilon | 3.49E−04 |
| 1561850_at | MGC15613 | hypothetical protein MGC15613 | 3.98E−04 |
| 218512_at | WDR12 | WD repeat domain 12 | 5.90E−04 |
| 228937_at | C13orf31 | chromosome 13 open reading frame 31 | 6.26E−04 |
| 238331_at | SPRN | shadow of prion protein homolog | 6.91E−04 |
| 227833_s_at | MBD6 | methyl-CpG binding domain protein 6 | 6.96E−04 |

The expression levels in the normal tissues 1 (8 samples) and the lesion tissues 1 (9 samples) with respect to each of these genes were input to the SVM. The accuracy of determining whether each sample was positive or negative was evaluated using the SVM containing the input expression levels in the 17 samples.

The result is shown in FIG. 19A. The result shows that the conventional method using genes other than those belonging to endometriosis-determining gene families identified the samples with lesion tissues and the samples with normal tissues at a sensitivity of 100% and a specificity of 100%.

(2-2) Evaluating the Reproducibility of the Conventional Determination Method

Data on the lesion tissues 2 (8 samples) and the normal tissues 2 (8 samples) were then used to evaluate the reproducibility of the conventional determination method using the ten genes. The determination was performed on these samples using the SVM to which the expression levels in the normal tissues 1 (8 samples) and the lesion tissues 1 (9 samples) were input in the section (2-1).

The result is shown in FIG. 19B. The result shows that for samples different from those used in the identification of endometriosis-determining gene families, the sensitivity of the conventional determination method was reduced to 0%, although the specificity was 100%. It is therefore apparent that the conventional determination method using genes other than those belonging to endometriosis-determining gene families is extremely more likely to misidentify endometriosis patients as healthy subjects than the determination method of the invention.

The results of Example 3 and Comparative Example 3 show that the determination method of the invention can achieve more accurate and more stable determination than conventional methods in which the presence of endometriosis is determined directly based on the levels of expression of gene transcription products in healthy subjects and endometriosis patients.

What is claimed is:

1. A computer program product, comprising:
a non-transitory computer readable medium; and
software instructions, on the computer readable medium, for enabling a computer to perform operations comprising:
receiving levels of expression of transcription products of genes in a biological sample obtained from a subject suspected of having a target disease, wherein the genes comprise at least one gene belonging to each of at least two disease-determining gene families related to the target disease;

obtaining values representing deviations by standardizing the levels of the expression based on the levels of expression of transcription products of the corresponding genes in a plurality of healthy subjects;

obtaining the average of values representing deviations with respect to the gene belonging to each of the disease-determining gene families;

determining whether or not the subject has the target disease by using the average; and outputting the result of the determination;

wherein the disease-determining gene families are gene families which were identified by the following steps:

measuring levels of expression of transcription products of genes in a biological sample obtained from each of a plurality of patients having the target disease and a plurality of healthy subjects;

obtaining values representing deviations for each of the patient by standardizing the levels of expression of the gene transcription products in each of the plurality of patients based on the levels of expression of transcription products of the corresponding genes in the healthy subjects;

obtaining values representing deviations for each of the healthy subjects by standardizing the 1 levels of expression of the gene transcription products in each of the healthy subjects;

classifying the genes, whose expression levels are measured, into at least two gene families using a classification system based on the function of molecules encoded by the genes;

obtaining, as an average for each gene family, the average of values representing deviations for the gene belonging to each of the gene families with respect to each of the patients and the healthy subjects;

obtaining a significance probability between the average for each gene family with respect to the patients and the average for each corresponding gene family with respect to the healthy subjects; and identifying the gene family as a disease-determining gene family related to the target disease, when the significance probability for the gene family is 0.05 or less.

2. The computer program product according to claim 1, wherein the computer readable medium comprises a hard disc.

3. The computer program product according to claim 1, wherein the computer readable medium comprises a CD-ROM and a DVD-ROM.

4. The computer program product according to claim 1, wherein the determination comprises a discriminant analysis method.

5. The computer program product according to claim 4, wherein the discriminant analysis method is a support vector machine, a linear discriminant analysis, a neural network, a k-neighborhood discriminator, a decision tree, or a random forest.

6. The computer program product according to claim 1, wherein the classification system based on the function of molecules encoded by the genes is Gene Ontology, Kyoto Encyclopedia of Genes and Genomes (KEGG), MetaCyc, GenMAPP, BioCarta, KeyMolnet, or Online Mendelian Inheritance in Man (OMIM).

7. The computer program product according to claim 1, wherein the target disease is selected from Crohn's disease, Huntington's disease, and endometriosis.

8. The computer program product according to claim 1, wherein
the target disease is Crohn's disease, and
the disease-determining gene families are at least two selected from a G protein-related gene family, a blood coagulation-related gene family, an oxidative stress-related gene family, a phagocytosis-related gene family, and fat oxidation-related gene family.

9. The computer program product according to claim 1, wherein
the target disease is Huntington's disease, and
the disease-determining gene families are at least two selected from a microtubule-related gene family, a mitochondria-related gene family, and a prostaglandin-related gene family.

10. The computer program product according to claim 1, wherein
the target disease is endometriosis, and
the disease-determining gene families are at least two selected from a cytokine synthesis process-related gene family, a cytokine-mediated signaling-related gene family, and an immunoglobulin-mediated immune response-related gene family.

11. The computer program product according to claim 1, wherein the step of measuring the levels of expression of gene transcription products comprises measuring the level of expression of at least one gene belonging to each of at least three disease-determining gene families.

12. The computer program product according to claim 8, wherein
the G protein-related gene family contains at least one gene selected from the group consisting of genes represented by the following gene symbols: GNG3, GNG7, GNA15, GNB5, GNAS, GNG5, GNG11, GNB1, and GNG4,
the blood coagulation-related gene family contains at least one gene selected from the group consisting of genes represented by the following gene symbols: GP1BA, GP1BB, ITGB3, GP9, and F13A1,
the oxidative stress-related gene family contains at least one gene selected from the group consisting of genes represented by the following gene symbols: GPX1, PTGS1, CLU, and PDLIM1,
the phagocytosis-related gene family contains at least one gene selected from the group consisting of genes represented by the following gene symbols: FCER1G, CLEC7A, VAMP7, and FCGR1A, and
the fat oxidation-related gene family contains at least one gene selected from the group consisting of genes represented by the following gene symbols: ACOX1, ADIPOR2, ADIPOR1, and ALOX12.

13. The computer program product according to claim 9, wherein
the microtubule-related gene family contains at least one gene selected from the group consisting of genes represented by the following gene symbols: DYNC1LI1, DYNLL1, DYNLT1, and DYNLT3,
the mitochondria-related gene family contains at least one gene selected from the group consisting of genes represented by the following gene symbols: ATP5F1, ATP5J, ATP5L, ATP5C1, ATP5O, COX6A1, COX7A2, CYCS, MRPL18, MRPS35, NDUFA4, NDUFA9, NDUFB1, NDUFB3, NDUFB5, NDUFC1, NDUFS4, TIMM17A, TIMM8B, TOMM20, TOMM7, UQCRH, UQCR, and UQCRQ, and the prostaglandin-related gene family contains at least one gene selected from the group consisting of genes represented by the following gene symbols: PTGER2, PTGER4, and PTGES3.

14. The computer program product according to claim 10, wherein the cytokine synthesis process-related gene family contains at least one gene selected from the group consisting of genes represented by the following gene symbols: CEBPE and CD28, the cytokine-mediated signaling-related gene family contains at least one gene selected from the group consisting of genes represented by the following gene symbols: EREG, STAT3, STAT5A, STAT5B, SOCS1, SOCS5, RELA, CEBPA, DUOX2, DUOX1, STAT4, ZNF675, IL2RB, IRAK3, KIT, LRP8, INFRSF1A, PLP2, TNFRSF1B, TGM2, CCRI, CCR2, PF4, CX3CL1, IL1R1, CSF2RB, CLCF1, and NUP85, and the immunoglobulin-mediated immune response-related gene family contains at least one gene selected from the group consisting of genes represented by the following gene symbols: 1GHG3, IGHM, CD74, FCER1G, BCL10, PRKCD, CD27, MYD88, and TLR8.

15. The computer program product according to claim 1, wherein the biological sample is blood.

16. A computer program product for enabling a computer to execute a method of identifying disease-determining gene families, the computer program product comprising:
a non-transitory computer readable medium; and
software instructions, on the computer readable medium, for enabling a computer to perform operations comprising:
receiving expression levels of transcription products of genes in a biological sample obtained from each of a plurality of patients having a target disease and a plurality of healthy subjects;
obtaining values representing deviations for each of the patients by standardizing each of the expression levels of the patients based on the expression levels of the healthy subjects;
obtaining values representing deviations for each of the healthy subjects by standardizing each of the expression levels of the patients based on the expression levels of the healthy subjects;
classifying the genes into at least two gene families using a classification system based on the function of molecules encoded by the genes;
obtaining, as an average for each gene family, the average of values representing deviations for the gene belonging to each of the gene families with respect to each of the patients and the healthy subjects;
obtaining a significance probability between the average for each gene family with respect to the patients and the average for each corresponding gene family with respect to the healthy subjects; and
identifying the gene family as a disease-determining gene family related to the target disease, when the significance probability for the gene family is 0.05 or less.

17. The computer program product according to claim 16, wherein the computer readable medium comprises a hard disc.

18. The computer program product according to claim 16, wherein the computer readable medium comprises a CD-ROM and a DVD-ROM.

19. A measuring system comprising:
a measuring apparatus that measures levels of expression of transcription products of genes in a biological sample; and
a computer including a hard disc that stores software instructions for enabling the computer to perform operations comprising:
receiving levels of expression of transcription products of genes in a biological sample obtained from a subject suspected of having a target disease from the measuring apparatus, wherein the genes comprise at least one gene belonging to each of at least two disease-determining gene families related to the target disease;
obtaining values representing deviations by standardizing the levels of the expression based on the levels of expression of transcription products of the corresponding genes in a plurality of healthy subjects;
obtaining the average of values representing deviations with respect to the gene belonging to each of the disease-determining gene families;
determining whether or not the subject has the target disease by using the average; and
outputting the result of the determination;
wherein the disease-determining gene families are gene families which were identified by the following steps:
receiving levels of expression of transcription products of genes in a biological sample obtained from each of a plurality of patients having the target disease and a plurality of healthy subjects from the measuring apparatus;
obtaining values representing deviations for each of the patient by standardizing the levels of expression of the gene transcription products in each of the plurality of patients based on the levels of expression of transcription products of the corresponding genes in the healthy subjects;
obtaining values representing deviations for each of the healthy subjects by standardizing the levels of expression of the gene transcription products in each of the healthy subjects;
classifying the genes into at least two gene families using a classification system based on the function of molecules encoded by the genes;
obtaining, as an average for each gene family, the average of values representing deviations for the gene belonging to each of the gene families with respect to each of the patients and the healthy subjects;
obtaining a significance probability between the average for each gene family with respect to the patients and the average for each corresponding gene family with respect to the healthy subjects; and
identifying the gene family as a disease-determining gene family related to the target disease, when the significance probability for the gene family is 0.05 or less.

20. A measuring system comprising:
a measuring apparatus that measures levels of expression of transcription products of genes in a biological sample; and
a computer including a hard disc that stores software instructions for enabling the computer to perform operations comprising:
receiving expression levels of transcription products of genes in a biological sample obtained from each of a plurality of patients having a target disease and a plurality of healthy subjects;

obtaining values representing deviations for each of the patients by standardizing each of the expression levels of the patients based on the expression levels of the healthy subjects;

obtaining values representing deviations for each of the healthy subjects by standardizing each of the expression levels of the patients based on the expression levels of the healthy subjects;

classifying the genes into at least two gene families using a classification system based on the function of molecules encoded by the genes;

obtaining, as an average for each gene family, the average of values representing deviations for the gene belonging to each of the gene families with respect to each of the patients and the healthy subjects;

obtaining a significance probability between the average for each gene family with respect to the patients and the average for each corresponding gene family with respect to the healthy subjects; and identifying the gene family as a disease-determining gene family related to the target disease, when the significance probability for the gene family is 0.05 or less.

* * * * *